(12) United States Patent
Ishihara et al.

(10) Patent No.: US 9,000,216 B2
(45) Date of Patent: Apr. 7, 2015

(54) IODOARENE DERIVATIVE, METHOD FOR MANUFACTURING OPTICALLY ACTIVE SPIROLACTONE COMPOUND BY USING THE SAME, AND METHOD FOR MANUFACTURING OPTICALLY ACTIVE CYCLOADDUCT

(75) Inventors: Kazuaki Ishihara, Nagoya (JP); Muhammet Uyanik, Nagoya (JP); Takeshi Yasui, Nagoya (JP)

(73) Assignee: National University Corporation Nagoya University, Nagoya-shi (JP)

( * ) Notice: Subject to any disclaimer, the term of this patent is extended or adjusted under 35 U.S.C. 154(b) by 0 days.

(21) Appl. No.: 14/002,574

(22) PCT Filed: Mar. 6, 2012

(86) PCT No.: PCT/JP2012/055679
§ 371 (c)(1),
(2), (4) Date: Aug. 30, 2013

(87) PCT Pub. No.: WO2012/121248
PCT Pub. Date: Sep. 13, 2012

(65) Prior Publication Data
US 2013/0338364 A1 Dec. 19, 2013

(30) Foreign Application Priority Data
Mar. 10, 2011 (JP) .................. 2011-052572

(51) Int. Cl.
| | | |
|---|---|---|
| *C07D 307/94* | (2006.01) | |
| *C07D 491/107* | (2006.01) | |
| *C07D 317/72* | (2006.01) | |
| *C07C 217/20* | (2006.01) | |
| *C07C 311/17* | (2006.01) | |
| *C07C 233/69* | (2006.01) | |
| *C07C 233/70* | (2006.01) | |
| *C07C 271/16* | (2006.01) | |

(Continued)

(52) U.S. Cl.
CPC ........... *B01J 31/0209* (2013.01); *C07C 217/20* (2013.01); *C07C 233/69* (2013.01); *C07C 233/70* (2013.01); *C07C 235/48* (2013.01); *C07C 271/16* (2013.01); *C07C 311/17* (2013.01); *C07D 307/94* (2013.01); *C07D 317/72* (2013.01); *C07D 491/107* (2013.01)

(58) Field of Classification Search
USPC ......................................... 514/654; 564/353
See application file for complete search history.

(56) References Cited

U.S. PATENT DOCUMENTS

| | | | | |
|---|---|---|---|---|
| 7,135,585 | B2 * | 11/2006 | Basarab et al. ............... | 558/392 |
| 7,396,844 | B1 * | 7/2008 | Takayanagi et al. .......... | 514/359 |
| 2010/0093720 | A1 | 4/2010 | Marsault et al. | |

FOREIGN PATENT DOCUMENTS

JP    A-2010-503620    2/2010

OTHER PUBLICATIONS

Chemical Abstracts Registry ID 1249688-98-9; entered Oct. 31, 2010.*

(Continued)

*Primary Examiner* — John Mabry
*Assistant Examiner* — Daniel Carcanague
(74) *Attorney, Agent, or Firm* — Oliff PLC

(57) ABSTRACT

An optically active spirolactone compound is highly enantioselectively produced by using an iodoarene derivative which can be synthesized easily and which is not racemized easily. A hypervalent iodine compound precursor (iodoarene derivative) which was able to be designed flexibly was synthesized from 2,6-dihydroxyiodoarene by using 1,2-aminoalcohol as a chiral source in short steps, a hypervalent iodine compound was prepared in a reaction system (in situ) by using a catalyst quantity of the resulting precursor in the presence of a stoichiometric quantity of m-CPBA, and a spirolactonization reaction of 3-(1-hydroxy-2-naphthyl)propionic acid was induced. As a result, a corresponding spirolactone compound was obtained at a high enantiomeric excess.

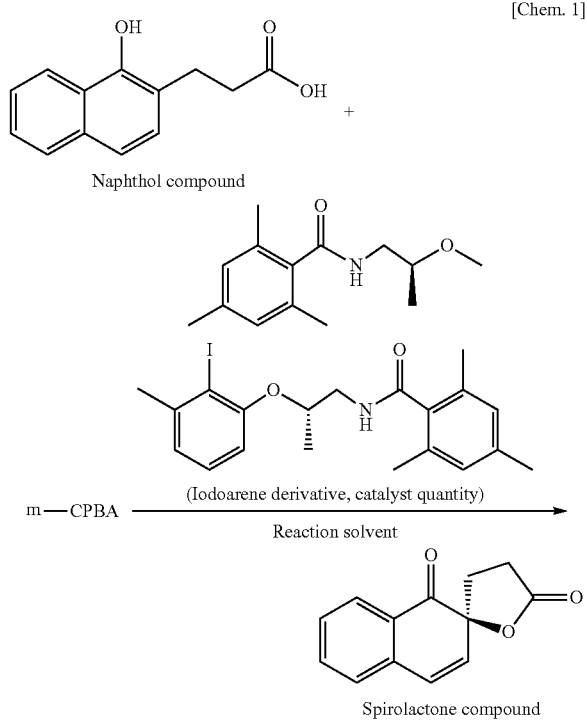

14 Claims, No Drawings

(51) Int. Cl.
*B01J 31/02* (2006.01)
*C07C 235/48* (2006.01)

(56) References Cited

OTHER PUBLICATIONS

Wojciechowski; J. Am. Chem. Soc. 2008, 130, pp. 12574-12575 & S1-S62.*
Drutu; Organic Letters, 2002, 4, 493-496.*
Uyanik et al., "Enantioselective Kita Oxidative Spirolactonization Catalyzed by In Situ Generated Chiral Hypervalent Iodine(III) Species," *Angewandte Chemie Int. Ed.*, 2010, pp. 2175-2177, vol. 49, Wiley-VCH Verlag GmbH & Co. KGaA.
Uyanik et al., "Chiral hypervalent iodine-catalyzed enantioselective oxidative Kita spirolactonization of 1-napthol derivatives and one-pot diastereo-selective oxidation to epoxyspirolactones," *Tetrahedron*, 2010, pp. 5841-5851, vol. 66, Elsevier Ltd.
International Search Report issued in International Patent Application No. PCT/JP2012/055679 dated Jun. 5, 2012.
Jul. 23, 2014 European Search Report issued in European Application No. 12754890.7.
Ioana Drutu et al., "Reactive Dienes: Intramolecular Aromatic Oxidation of 3-(2-Hydroxyphenyl)-propionic Acids", *Organic Letters.*, vol. 4, No. 4, Jan. 31, 2002, pp. 493-496.
STN Registry, ACS, 1249688 98 9/RN, Entered Oct. 31, 2010.

* cited by examiner

IODOARENE DERIVATIVE, METHOD FOR MANUFACTURING OPTICALLY ACTIVE SPIROLACTONE COMPOUND BY USING THE SAME, AND METHOD FOR MANUFACTURING OPTICALLY ACTIVE CYCLOADDUCT

TECHNICAL FIELD

The present invention relates to an iodoarene derivative, a method for manufacturing an optically active spirolactone compound by using the same, and a method for manufacturing an optically active cycloadduct.

BACKGROUND ART

In NPL 1, the present inventors designed a hypervalent iodine compound precursor, which contained 2,6-dihydroxyiodobenzene as a base skeleton and which was able to be designed flexibly by using lactic acid as a chiral source, from a commercially available product in 3 to 4 steps. A hypervalent iodine compound was prepared in a reaction system (in situ) by using a catalyst quantity of the resulting hypervalent iodine compound precursor in the presence of a stoichiometric quantity of m-CPBA, and a catalytic enantioselective dearomatization type oxidation reaction of a 1-naphthol derivative was induced. As a result, a spirolactone compound was obtained at high chemical yield and enantiomeric excess.

CITATION LIST

Non Patent Literature

NPL 1: Angewandte Chemie International Edition (Angew. Chem. Int. Ed.), 2010, vol. 49, p. 2175-2177

SUMMARY OF INVENTION

Technical Problem

Although such a hypervalent iodine compound precursor can be synthesized easily, a carbonyl group is present adjacent to a chiral carbon atom. Therefore, the stability may be insufficient because racemization occurs easily on the basis of keto-enol tautomerism.

The present invention has been made to solve the above-described problems, and a main object is to highly enantioselectively produce an optically active spirolactone compound by using a stable iodoarene derivative which can be synthesized easily.

Solution to Problem

In order to achieve the above-described object, the present inventors synthesized a hypervalent iodine compound precursor, which was able to be designed flexibly, from 2,6-dihydroxyiodobenzene by using 1,2-aminoalcohol as a chiral source in short steps, prepared a hypervalent iodine compound in a reaction system (in situ) by using a catalyst quantity of the resulting precursor in the presence of a stoichiometric quantity of m-CPBA, and attempted to induce a spirolactonization reaction of 3-(1-hydroxy-2-naphthyl)propionic acid. As a result, it was found that an optically active spirolactone compound was obtained at a high enantiomeric excess, and the present invention has been completed.

An iodoarene derivative of the present invention is represented by Formula (1). In Formula (1), A represents a monovalent iodine atom or a trivalent iodine atom having two ligands, $R^1$ and $R^2$ represent independently a hydrogen atom, an alkyl group, an aryl group, —$COR^a$, or —$SO_2R^a$ ($R^a$ represents an alkyl group, a cycloalkyl group, an aryl group, or an alkoxy group) or bond to each other to form a lactam, R represents a hydrogen atom, an alkyl group, or —$OCH(R^7)CH(R^8)NR^5R^6$, $R^5$ and $R^6$ represent independently a hydrogen atom, an alkyl group, an aryl group, —$COR^b$, or —$SO_2R^b$ ($R^b$ represents an alkyl group, a cycloalkyl group, an aryl group, or an alkoxy group) or bond to each other to form a lactam, $R^4$ and $R^8$ represent hydrogen atoms, $R^3$ and $R^7$ represent independently an alkyl group, a cycloalkyl group, an arylmethyl group, or an aryl group, and both configurations of asymmetric carbon atoms bonding to $R^3$ and $R^7$ are R or both the configurations are S, or $R^3$ and $R^7$ represent hydrogen atoms, $R^4$ and $R^8$ represent independently an alkyl group, a cycloalkyl group, an arylmethyl group, or an aryl group, and both configurations of asymmetric carbon atoms bonding to $R^4$ and $R^8$ are R or both the configurations are S, and Z represents a hydrogen atom, an electron-withdrawing group, or an electron-donating group.

[Chem. 1]

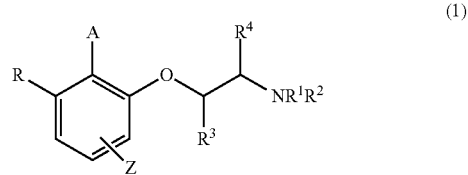

(1)

A method for manufacturing an optically active spirolactone compound, according to the present invention, is (A) a method including the step of mixing a phenol derivative, an iodoarene derivative and a peroxycarboxylic acid in such a way that the iodoarene derivative is a catalyst quantity relative to the phenol derivative and the peroxycarboxylic acid is more than or equal to a stoichiometric quantity relative to the phenol derivative to induce a reaction, so that an optically active spirolactone compound is obtained in which a OH group of the phenol derivative is converted to an oxo group (=O) and dearomatized to have spiro-bonding of lactone rings, wherein the phenol derivative has one of two adjacent carbon atoms constituting an aromatic ring bonded to a OH group and the other bonded to -Q-COOH (Q represents —$(CH_2)_n$— (n represents 2 or 3), —$O(CH_2)_m$— (m represents 1 or 2), —$CH_2OCH_2$—, —$(CH_2)_kCH=CH$— (k represents 0 or 1 and an olefin part is cis), —$(CH_2)_kC=C$— (k represents 0 or 1 and C≡C represents adjacent two carbon atoms of a benzene ring or a naphthalene ring), —OCH=CH— (an olefin part is cis), or —OC≡C— (C≡C represents adjacent two carbon atoms of a benzene ring or a naphthalene ring)), the iodoarene derivative is the derivative, in which A represents a monovalent iodine atom, and the peroxycarboxylic acid is capable of oxidizing the iodoarene derivative to convert to a hypervalent iodine compound, or (B) a method including the step of mixing a phenol derivative and iodoarene derivative in such a way that the iodoarene derivative is more than or equal to a stoichiometric quantity relative to the phenol derivative to induce a reaction, so that an optically active spirolactone compound is obtained in which a OH group of the phenol derivative is converted to an oxo group (=O) and dearomatized to have spiro-bonding of lactone rings, wherein the phenol derivative has one of two adjacent carbon atoms constituting an aromatic ring bonded to a OH group and the other bonded to -Q-COOH (Q is as described above), and the iodoarene derivative is the derivative in which A represents a trivalent iodine atom.

Advantageous Effects of Invention

The iodoarene derivative according to the present invention can be synthesized from 2-iodoresorcinol, 2-iodophenol, and derivatives thereof by using 1,2-aminoalcohol as a chiral source in short steps (for example, 3 steps). Therefore, mass-production can be performed inexpensively and there is high economy. In addition, stability is high because there is no fear of racemization of asymmetric center carbon due to tautomerism. This iodoarene derivative is utilized for enantioselective dearomatization type oxidation of the phenol derivative in which one of two adjacent carbon atoms constituting an aromatic ring is bonded to a OH group and the other is bonded to -Q-COOH (Q is as described above). Furthermore, the structure can be flexibly designed. Consequently, for example, screening is performed by using various iodoarene derivatives on a reaction substrate basis, and a structure suitable for the reaction substrate can be found easily. Moreover, the stability is very high as described above, so that recovery and reuse are also possible after the dearomatization type oxidation is finished.

According to the method for manufacturing an optically active spirolactone compound of the present invention, the optically active spirolactone compound can be highly enantioselectively produced by using the above-described iodoarene derivative. In this regard, the iodoarene derivative in which A represents a monovalent iodine atom functions as a catalyst precursor. At that time, it is believed that the reaction proceeds as described below. That is, when this iodoarene derivative, the peroxycarboxylic acid (or hydrogen peroxide or other peracid), and the reaction substrate are mixed, the iodoarene derivative is oxidized by the peroxycarboxylic acid to become a catalyst (hypervalent iodine compound). The catalyst oxidizes and, at the same time, dearomatizes the phenol derivative so as to convert to a corresponding spirolactone compound. In addition, the iodoarene derivative in itself is reduced and is returned to the catalyst precursor, that is, the iodoarene derivative, again. Meanwhile, the iodoarene derivative in which A represents a trivalent iodine atom oxidizes and, at the same time, dearomatizes the phenol derivative so as to convert to a corresponding spirolactone compound. In addition, the iodoarene derivative in itself is reduced and is returned to the iodoarene derivative in which A represents I.

DESCRIPTION OF EMBODIMENTS

The iodoarene derivative according to the present invention is represented by Formula (1) described above, where A represents a monovalent iodine atom or a trivalent iodine atom having two ligands, $R^1$ and $R^2$ represent independently a hydrogen atom, an alkyl group, an aryl group, —$COR^a$, or —$SO_2R^a$ ($R^a$ represents an alkyl group, a cycloalkyl group, an aryl group, or an alkoxy group) or bond to each other to form a lactam, R represents a hydrogen atom, an alkyl group, or —$OCH(R^7)CH(R^8)NR^5R^6$, $R^5$ and $R^6$ represent independently a hydrogen atom, an alkyl group, an aryl group, —$COR^b$, or —$SO_2R^b$ ($R^b$ represents an alkyl group, a cycloalkyl group, an aryl group, or an alkoxy group) or bond to each other to form a lactam, $R^4$ and $R^8$ represent hydrogen atoms, $R^3$ and $R^7$ represent independently an alkyl group, a cycloalkyl group, an arylmethyl group, or an aryl group, and both configurations of asymmetric carbon atoms bonding to $R^3$ and $R^7$ are R or both the configurations are S, or $R^3$ and $R^7$ represent hydrogen atoms, $R^4$ and $R^8$ represent independently an alkyl group, a cycloalkyl group, an arylmethyl group, or an aryl group, and both configurations of asymmetric carbon atoms bonding to $R^4$ and $R^8$ are R or both the configurations are S, and Z represents a hydrogen atom, an electron-withdrawing group, or an electron-donating group.

Here, the ligand is not specifically limited, and examples include an acyloxy group and a hydroxy group. Examples of acyloxy groups include acyloxy groups having the carbon number of 2 to 12, e.g., an acetoxy group, a benzoyloxy group, and a p-chlorobenzoyloxy group. In this regard, the two ligands bonding to the trivalent iodine atom may be the same or different.

The alkyl group is not specifically limited, and examples include alkyl groups which may have a branch and which have the carbon number of 1 to 4, e.g., a methyl group, an ethyl group, a propyl group, an isopropyl group, a butyl group, an isobutyl group, a sec-butyl group, and a tert-butyl group.

The cycloalkyl group is not specifically limited, and examples include cycloalkyl groups having the carbon number of 3 to 7, e.g., a cyclopropyl group, a cyclobutyl group, a cyclopentyl group, a cyclohexyl group, and a cycloheptyl group.

The aryl group is not specifically limited, and examples include a phenyl group, a naphthyl group, and those groups in which at least one hydrogen atom has been substituted with a substituent. Examples of substituents include a halogen atom, an alkyl group, a cycloalkyl group, and a perfluoroalkyl group. Here, as for the alkyl group and the cycloalkyl group, the groups described above as examples are mentioned. As for the perfluoroalkyl groups, a trifluoromethyl group, a pentafluoroethyl group, and the like are mentioned. Specific examples of the above-described aryl groups include a phenyl group, a 2-tolyl group, a 3-tolyl group, a 4-tolyl group, a 2-trifluoromethyl phenyl group, a 3-trifluoromethyl phenyl group, a 4-trifluoromethyl phenyl group, a 2-methoxyphenyl group, a 3-methoxyphenyl group, a 4-methoxyphenyl group, a 2,3-xylyl group, a 2,4-xylyl group, a 2,5-xylyl group, a 2,6-xylyl group, a 3,4-xylyl group, a 3,5-xylyl group, a 2,3-bis(trifluoromethyl)phenyl group, a 2,4-bis(trifluoromethyl) phenyl group, a 2,5-bis(trifluoromethyl)phenyl group, a 2,6-bis(trifluoromethyl)phenyl group, a 3,4-bis(trifluoromethyl) phenyl group, a 3,5-bis(trifluoromethyl)phenyl group, a 2,3-dimethoxyphenyl group, a 2,4-dimethoxyphenyl group, a 2,5-dimethoxyphenyl group, a 2,6-dimethoxyphenyl group, a 3,4-dimethoxyphenyl group, a 3,5-dimethoxyphenyl group, a 2,3-diethylphenyl group, a 2,4-diethylphenyl group, a 2,5-diethylphenyl group, a 2,6-diethylphenyl group, a 3,4-diethylphenyl group, a 3,5-diethylphenyl group, a 2,3-di-tert-butylphenyl group, a 2,4-di-tert-butylphenyl group, a 2,5-di-tert-butylphenyl group, a 2,6-di-tert-butylphenyl group, a 3,4-di-tert-butylphenyl group, a 3,5-di-tert-butylphenyl group, a 2,4,6-trimethylphenyl group (mesityl group), a 2,3,4-trimethylphenyl group, a 2,3,5-trimethylphenyl group, a 2,3,6-trimethylphenyl group, a 3,4,5-trimethylphenyl group, a 2,4,6-triisopropylphenyl group, a 2,3,4-triisopropylphenyl group, a 2,3,5-triisopropylphenyl group, a 2,3,6-triisopropylphenyl group, a 3,4,6-triisopropylphenyl group, a 1-naphthyl group, a 2-naphthyl group, a pentafluorophenyl group, and a 9-anthracenyl group. The same goes for the aryl of the arylmethyl group.

Examples of alkoxy groups include alkoxy groups which may have a branch and which have the carbon number of 1 to 4, e.g., a methoxy group, an ethoxy group, a propoxy group, an isopropoxy group, a n-butoxy group, an isobutoxy group, a sec-butoxy group, and a tert-butoxy group.

In the case where $R^1$ and $R^2$ or $R^5$ and $R^6$ bond to each other to form a lactam, examples of lactams include five-membered ring lactams, six-membered ring lactams, and seven-membered ring lactams.

The m position, the p position, or both of them relative to the iodine atom are bonded to Z. Examples of electron-withdrawing groups include a chlorine atom, a bromine atom, a cyano group, and a nitro group. Examples of electron-donating groups include an alkyl group and an alkoxy group. As for the alkyl group and the alkoxy group, the groups described above as examples are mentioned.

The iodoarene derivative according to the present invention is used for enantioselective dearomatization type oxidation of the phenol derivative in which one of two adjacent carbon atoms constituting an aromatic ring is bonded to a OH group and the other is bonded to -Q-COOH (Q is as described above). In that case, it is preferable that the iodoarene derivative (referred to as Type 1) be represented by Formula (1), where R represents $R^5R^6NCH(R^8)CH(R^7)O—$, $R^1$, $R^4$, $R^5$, and $R^8$ represent hydrogen atoms, $R^2$ and $R^6$ represent independently —$COR^a$ ($R^a$ represents an aryl group), and $R^3$ and $R^7$ represent independently an alkyl group or the iodoarene derivative (referred to as Type 2) be represented by Formula (1), where R represents $R^5R^6NCH(R^8)CH(R^7)O—$, $R^1$, $R^3$, $R^5$, and $R^7$ represent hydrogen atoms, $R^2$ and $R^6$ represent independently —$COR^a$ ($R^a$ represents an aryl group), and $R^4$ and $R^8$ represent independently an alkyl group. Consequently, the optically active spirolactone compound can be produced from the phenol derivative at a high enantiomeric excess. It is more preferable that —$COR^a$ ($R^a$ represents an aryl group) be a 2,4,6-trimethylphenylcarbonyl group or a 9-anthranylcarbonyl group. Meanwhile, it is preferable that Z be a hydrogen atom or an alkyl group, and in the case of the alkyl group, it is preferable to be bonded to the p position relative to the iodine atom. A structural formula representing an example of Type 1 and a structural formula representing an example of Type 2 are as described below.

[Chem. 2]

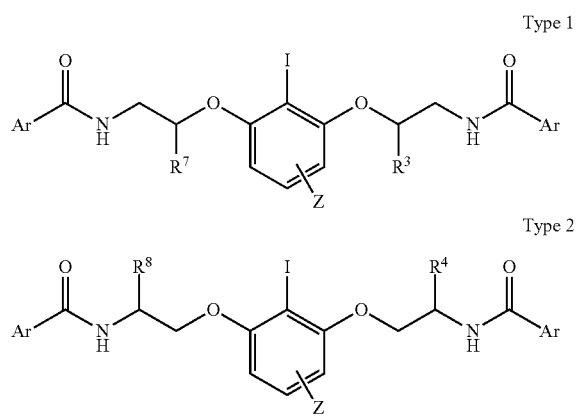

In the case where the structure of the iodoarene derivative, which serves as a reaction promoter, according to the present invention is optimized in accordance with the structure of the phenol derivative, which serves as a reaction substrate, various types of iodobenzene represented by Formula (1), in which $R^1$ to $R^8$ are changed, may be synthesized, optically active spirolactone compounds may be produced from the reaction substrate by using them, and a structure which leads to an optimum result may be selected.

The method for manufacturing the optically active spirolactone compound according to the present invention is (A) a method including the step of mixing a phenol derivative, an iodoarene derivative and a peroxycarboxylic acid in such a way that the iodoarene derivative is a catalyst quantity relative to the phenol derivative and the peroxycarboxylic acid is more than or equal to a stoichiometric quantity relative to the phenol derivative to induce a reaction, so that an optically active spirolactone compound is obtained in which a OH group of the phenol derivative is converted to an oxo group (=O) and dearomatized to have spiro-bonding of lactone rings, wherein the phenol derivative has one of two adjacent carbon atoms constituting an aromatic ring bonded to a OH group and the other bonded to -Q-COOH, the iodoarene derivative is the derivative, in which A represents a monovalent iodine atom, and the peroxycarboxylic acid is capable of oxidizing the iodoarene derivative to convert to a hypervalent iodine compound, or (B) a method including the step of mixing a phenol derivative and iodoarene derivative in such a way that the iodoarene derivative is more than or equal to a stoichiometric quantity relative to the phenol derivative to induce a reaction, so that an optically active spirolactone compound is obtained in which a OH group of the phenol derivative is converted to an oxo group (=O) and dearomatized to have spiro-bonding of lactone rings, wherein the phenol derivative has one of two adjacent carbon atoms constituting an aromatic ring bonded to a OH group and the other bonded to -Q-COOH (Q is as described above), and the iodoarene derivative is the derivative in which A represents a trivalent iodine atom.

In the phenol derivative used in this manufacturing method, one of two adjacent carbon atoms constituting an aromatic ring is bonded to a OH group and the other is bonded to -Q-COOH. Here, Q represents —$(CH_2)_n$— (n represents 2 or 3), —$O(CH_2)_m$— (m represents 1 or 2), —$CH_2OCH_2$—, —$(CH_2)_kCH=CH$— (k represents 0 or 1 and an olefin part is cis), —$(CH_2)_kC≡C$— (k represents 0 or 1 and C≡C represents adjacent two carbon atoms of a benzene ring or a naphthalene ring), —$OCH=CH$— (an olefin part is cis), or —$OC≡C$— (C≡C represents adjacent two carbon atoms of a benzene ring or a naphthalene ring). In the benzene ring or the naphthalene ring, at least one hydrogen atom may be substituted with a substituent. Examples of substituents include an alkyl group, a trialkylsilyl group, a triarylsilyl group, an alkyldiarylsilyl group, an aryldialkylsilyl group, a cycloalkyl group, an alkoxy group, an aryl group, an aromatic alkyl group, a halogen group, an alkyl group having an ether bond, an arylcarbonyl group, an alkylcarbonyl group, a cyano group, and a nitro group. Specific examples thereof will be described in the following paragraph.

Examples of phenol derivatives used in this manufacturing method include phenol compounds, e.g., 3-(2-hydroxyphenyl)propionic acid, 4-(2-hydroxyphenyl)butanoic acid, 2-hydroxyphenoxyacetic acid, and 3-(2-hydroxyphenoxy)propionic acid; and naphthol compounds, e.g., 3-(1-hydroxy-2-naphthyl)propionic acid, 4-(1-hydroxy-2-naphthyl)butanoic acid, 1-hydroxy-2-naphthoxyacetic acid, 1-hydroxy-2-naphthoxypropionic acid, 3-(2-hydroxy-1-naphthyl)propionic acid, 4-(2-hydroxy-1-naphthyl)butanoic acid, 2-hydroxy-1-naphthoxyacetic acid, and 2-hydroxy-1-naphthoxypropionic acid. At least one of positions 3 to 5 (in particular, position 5, that is, a carbon atom adjacent to the hydroxyl group) of 2-hydroxyphenyl of the phenol compound may have a substituent. At least one of positions 3 to 8 of 1-hydroxy-2-naphthyl and 2-hydroxy-1-naphthyl of the naphthol compound may have a substituent. Examples of substituents include alkyl groups, e.g., a methyl group, an ethyl group, a propyl group, an isopropyl group, a n-butyl group, an isobutyl group, a sec-butyl group, and a tert-butyl group; trialkylsilyl groups, e.g., a trimethylsilyl group, a triethylsylyl group, a triisopropylsylyl group, a diethylisopropylsylyl group, a dimethylisopropylsylyl group, a di-tert-butylmethylsylyl group, an isopropyldimethylsylyl group, and a tert-butyldimethylsylyl group; triarylsilyl groups, e.g., a triphenylsylyl group; alkyldiarylsylyl groups, e.g., a diphenylmethylsylyl group and a tert-butyldiphenylsylyl group; aryldialkylsylyl groups, e.g., a dimethylphenylsylyl group; cycloalkyl groups, e.g., a cyclopropyl group, a cyclobutyl group, a cyclopentyl group, and a cyclohexyl group; alkoxy groups, e.g., a methoxy group, an ethoxy group, a propoxy group, and an isopropoxy group; aryl groups, e.g., a phenyl group; aromatic alkyl groups, e.g., a benzyl group; halogen groups, e.g., a chloro group and a bromo group; alkyl groups having an ether bond, e.g., benzyloxymethyl; arylcarbonyl groups, e.g., a phenylcarbonyl group and a 4-bromophenylcarbonyl group; and alkylcarbonyl groups, e.g., a methylcarbonyl group and an ethylcarbonyl group. Other examples include a cyano group and a nitro group. Among them, in consideration of the reactivity, the naphthol compound is preferable rather than the phenol compound, and a naphthol compound in which a OH group is bonded to position 1 and -Q-COOH is bonded to position 2 and a naphthol compound in which -Q-COOH is bonded to position 1 and a OH group is bonded to position 2 are more preferable. Meanwhile, in consideration of the stability of the spirolactone compound which is a reaction product, the number of atoms between an aromatic ring and COOH is preferably 2 because the five-membered ring lactone is more stable than the six-membered ring lactone.

As for the iodoarene derivative used for the above-described manufacturing method, a compound represented by Formula (1) described above is employed.

Examples of peroxycarboxylic acids used for the above-described manufacturing method (A) include peracetic acid, perbenzoic acid, and m-chloroperbenzoic acid (m-CPBA). Among them, perbenzoic acid and m-CPBA are preferable because of ease of handling. In this regard, a commercially available m-CPBA having a low-purity (purity about 77%) may be used without purification (the remainder includes mCBA, water and the like), or such a commercially available product may be used after purification. Meanwhile, the peroxycarboxylic acid is a peracid produced by substituting a hydroxyl group of carboxylic acid with a hydroperoxy group and is generated by reacting carboxylic acid with a peroxide, e.g., hydrogen peroxide. Therefore, carboxylic acid and a peroxide may be put into a reaction system in combination and the peroxycarboxylic acid may be generated on the spot instead of putting the peroxycarboxylic acid into the reaction system.

In the reaction process of the above-described manufacturing method (A), the peroxycarboxylic acid oxidizes the iodoarene derivative in which A represents a monovalent iodine atom to convert to a hypervalent iodine compound (iodoarene derivative in which A represents a trivalent iodine atom having two ligands) and, in addition, the peroxycarboxylic acid in itself is reduced to a carboxylic acid. On the other hand, the hypervalent iodine compound converts the phenol derivative to a spirolactone compound and, in addition, the hypervalent iodine compound in itself is reduced to return to the iodoarene derivative in which A represents a monovalent iodine atom. Therefore, it is enough that the iodoarene derivative in which A represents a monovalent iodine atom is a catalyst quantity. However, it is necessary that the peroxycarboxylic acid be more than or equal to a stoichiometric quantity relative to the phenol derivative. Consequently, preferably 0.5 to 50 percent by mole of iodoarene derivative is used relative to the phenol derivative. Less than 0.5 percent by mole is not preferable because the reaction proceeds slowly and the reaction time increases. More than 50 percent by mole is not preferable from the viewpoint of economy because the yield and the enantiomeric excess do not increase significantly. In consideration of compatibility between the above-described reactivity and the economy, use of 5 to 30 percent by mole is more preferable. Meanwhile, as for the usage of the peroxycarboxylic acid, it is enough that equal moles are used relative to the phenol derivative. However, in consideration of smoother proceeding of the reaction, use of 1.1 to 1.5 times the moles of phenol derivative is preferable.

In the reaction process of the above-described manufacturing method (B), the hypervalent iodine compound converts the phenol derivative to a spirolactone compound and, in addition, the hypervalent iodine compound in itself is reduced to the iodoarene derivative in which A represents a monovalent iodine atom. Therefore, it is necessary that the hypervalent iodine compound be more than or equal to a stoichiometric quantity relative to the phenol derivative. The hypervalent iodine compound is produced by isolating a reaction product of the iodoarene derivative which is a monovalent iodine atom and the peroxycarboxylic acid. In this manufacturing method (B), it is not necessary that the peroxycarboxylic acid is present in the reaction system. Consequently, in the case where a reaction substrate which reacts with the peroxycarboxylic acid easily is used or in the case where the resulting spirolactone compound reacts with the peroxycarboxylic acid and is converted to another compound, it is preferable that the manufacturing method (B) be adopted rather than the manufacturing method (A). Conversely, in the case where isolation of the hypervalent iodine compound is difficult, it is preferable that the manufacturing method (A) be adopted.

In the above-described manufacturing methods (A) and (B), various reaction solvents can be utilized. Examples of usable reaction solvents include halogenated alkanes, e.g., methylene chloride, chloroform, carbon tetrachloride, and 1,2-dichloroethane; aromatic hydrocarbons, e.g., benzene, toluene, xylene, and benzene chloride; nitroalkanes, e.g., nitromethane; nitrile based solvents, e.g., acetonitrile and propionitrile; ester based solvents, e.g., methyl acetate and ethyl acetate; fluorine based alcohols, e.g., 2,2,2-trifluoroethanol (TEE) and 1,1,1,3,3,3-hexafluoro-2-propanol (HFIP); and mixtures thereof. Among them, in consideration of the yield and the enantiomeric excess, halogenated alkanes, nitroalkanes, esters, fluorine based alcohols, and mixtures thereof are preferable. The usage of the reaction solvent is not specifically limited. For example, it is set in such a way that the concentration of the phenol derivative becomes 0.01 to 1 M, and preferably 0.02 to 0.2 M. Meanwhile, a naphthol compound or phenol compound in which a OH group is bonded to position 1 and -Q-COOH is bonded to position 2 is used as the phenol derivative, it is preferable that alcohol be added to the reaction solvent because the enantiomeric excess is improved. Preferable examples of alcohols include alcohols having the carbon number of 1 to 4, e.g., methanol, ethanol, n-propanol, isopropanol, n-butanol, isobutanol, sec-butanol, and tert-butanol, and among them, ethanol is more preferable. The amount of addition of the alcohol is 1 to 50 equivalents relative to the phenol derivative, and preferably 3 to 10 equivalents are employed. In this regard, in the case where a mixture solvent of the halogenated alkane and the fluorine based alcohol is used or a mixed solvent of the halogenated alkane and the nitroalkane is used, at least one of the yield and the enantiomeric excess may be improved depending on the reaction substrate.

The temperatures of the above-described manufacturing methods (A) and (B) are not specifically limited, but −50° C. to 50° C. is preferable and −20° C. to 40° C. are more preferable. Lower than −50° C. is not preferable because the reaction rate becomes too low. Higher than 50° C. is not preferable because the enantioselectivity may be degraded, although the reaction rate is improved. Meanwhile, it is not necessary that the atmosphere of the reaction system be specified as an inert atmosphere of a nitrogen gas, an argon gas, or the like. The reaction proceeds without problem even in an air atmosphere.

The method for manufacturing an optically active cycloadduct, according to the present invention, is a method for obtaining an optically active [4+2]cycloadduct by reacting the optically active spirolactone compound obtained by the above-described method for manufacturing an optically active spirolactone compound with a dienophile without isolation. This manufacturing method is effective especially in the case where an optically active spirolactone compound is unstable. Examples of dienophiles include alkenes and alkynes. Such a dienophile may be added after the optically active spirolactone compound has been generated in the system, but it is preferable that the dienophile is included in the system together with the phenol derivative from the start in consideration of the operability. On the other hand, in consideration of the chemical yield, it is preferable that addition be performed after the optically active spirolactone compound have been generated in the system. In this regard, the [4+2]cycloaddition reaction be performed at a temperature higher than the reaction temperature in production of the optically active spirolactone compound. The dienophile is not specifically limited. Examples include α,β-unsaturated aldehydes, e.g., acrolein; α,β-unsaturated ketones, e.g., methyl vinyl ketone and quinone; α,β-unsaturated carboxylic acid esters, e.g., methyl acrylate and ethyl acrylate; and α,β-unsaturated acid anhydrides, e.g., maleic anhydride.

As a matter of course, the present invention is not limited to the above-described embodiments and can be executed in various forms within the technical scope of the present invention.

EXAMPLES

In the following examples, the $^1$H NMR spectrum was measured with a JEOL ECS-400 (400 MHz) spectrometer and the $^{13}$C NMR spectrum was measured with a JEOL ECS-400 (100 MHz) spectrometer. The optical purity of the reaction product was measured with a Shimadzu LC-10 apparatus on the basis of high performance liquid chromatography (HPLC) by using 4.6 mm×25 cm Daicel CHIRALCEL OD-H, AD-H, AS-H, and AD-3. The proceeding of the reaction was monitored on the basis of the thin layer chromatography (TLC) by using a Merck precoated TLC plate (silica gel 60, GF254, 0.25 mm).

[1] Synthesis of Iodoarene Derivative
[1-1] Synthesis of Iodoarene Derivative Type 1

Iodoarene derivatives A to M and R to V were synthesized following the reaction formulae described below. They are referred to as Type 1, in which a substituent is bonded to the carbon atom on the oxygen side of the ethylene chain between the oxygen atom and the nitrogen atom in the side chain. All the iodoarene derivatives A to M and R to V correspond to the examples according to the present invention. In this regard, 2-iodoresorcinols were synthesized on the basis of the method described in a literature (Org. Syn., 2007, vol. 84, p 272).

[Chem. 3]

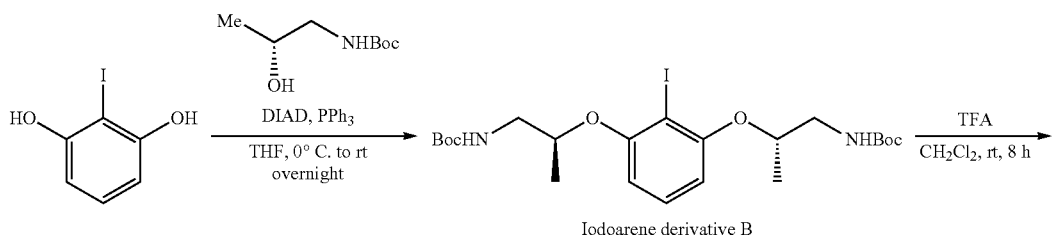

Iodoarene derivative B

-continued
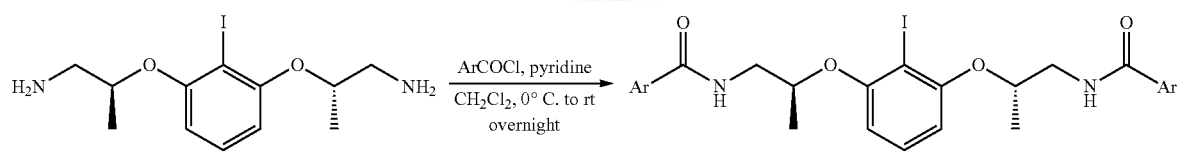
Iodoarene derivative A → Iodoarene derivative C—G, I, K—M
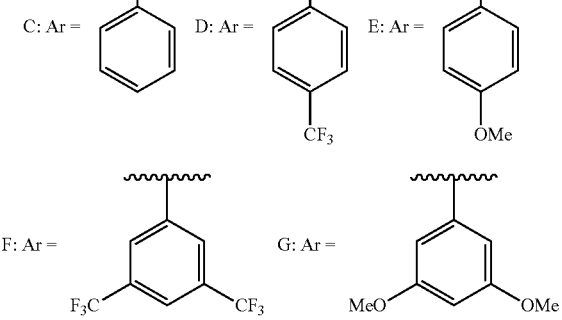
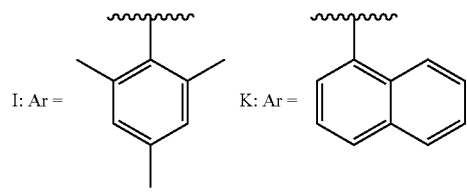
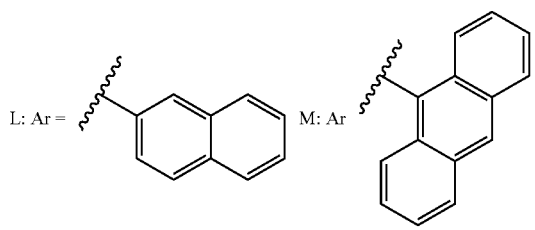
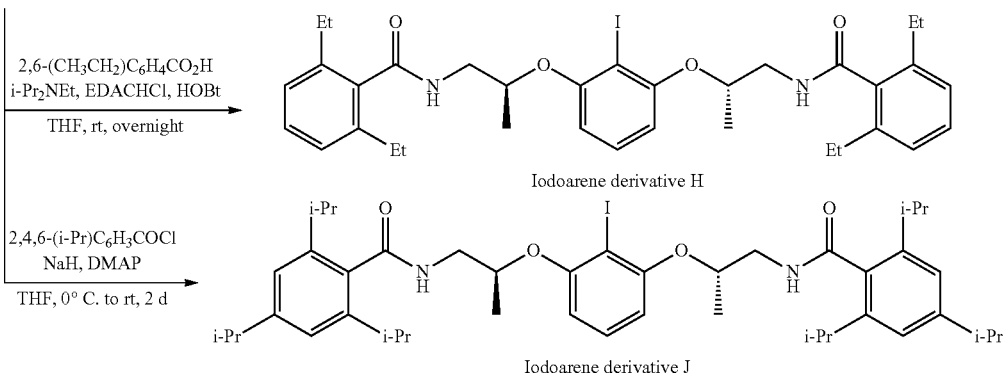
Iodoarene derivative H
Iodoarene derivative J
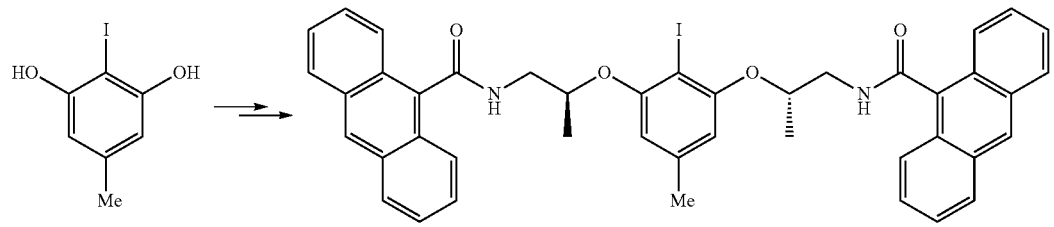
Iodoarene derivative R

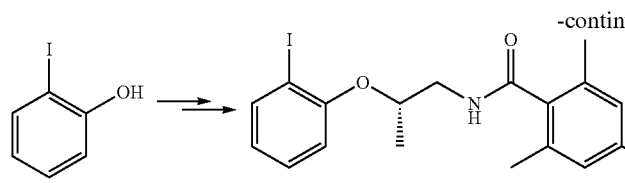

Iodoarene derivative S

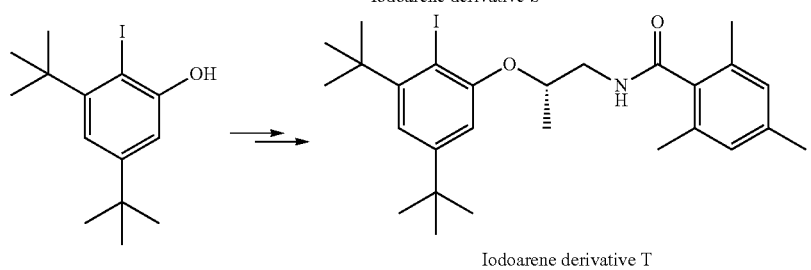

Iodoarene derivative T

Synthesis of Iodoarene Derivatives A and B

A solution was prepared by dissolving 2-iodoresorcinol (0.94 g, 4.0 mmol), PPh$_3$ (2.62 g, 10.0 mmol), and (R)-1-amino-2-propanol in which a nitrogen atom was protected by a Boc group (1.75 g, 10.0 mmol) into THF (13.0 mL). Diisopropylazodicarboxylate (DIAD, 1.9-M toluene solution, 10.0 mmol, 5.3 mL) was added to the resulting solution at 0° C. gradually. The resulting reaction mixed solution was stood and the temperature was returned to room temperature. After agitation was performed for a night, the mixture was concentrated in a vacuum. The residue was treated by silica gel flash column chromatography (dissolution medium hexane-EtOAc=10:1 to 4:1 (v/v)) to obtain Iodoarene derivative B (1.83 g, 3.3 mmol) at a yield of 83%. The spectrum data of Iodoarene derivative B are as described below.

$^1$H NMR (CDCl$_3$, 400 MHz) δ 1.34 (d, J=6.0 Hz, 6H), 1.43 (s, 18H), 3.23-3.38 (m, 2H), 3.40-3.59 (m, 2H), 4.40-4.59 (m, 2H), 5.10-5.23 (m, 2H), 6.50 (d, J=8.0 Hz, 2H), 7.20 (t, J=8.0 Hz, 1H); $^{13}$C NMR (CDCl$_3$, 100 MHz) δ 17.0 (2C), 28.2 (6C), 45.4 (2C), 77.2 (2C), 79.1 (2C), 82.0, 106.9 (2C), 129.6, 155.9 (2C), 157.7 (2C).

Trifluoroacetic acid (TFA, 1.1 mL, 15 mmol) was added to a solution in which Iodoarene derivative B (1.83 g, 3.3 mmol) was dissolved into CH$_2$Cl$_2$ (15.0 mL), and agitation was performed at room temperature for 8 hours. The resulting reaction mixed solution was cooled to 0° C. and was quenched with 2-N NaOH. Extraction was performed with chloroform. An organic layer was dried with anhydrous Na$_2$SO$_4$, and the solvent was removed by distillation in a vacuum, so as to obtain Iodoarene derivative A (1.16 g, 3.3 mmol) at a yield of more than 99% and the purity of more than 99% (on the basis of $^1$H NMR analysis). The spectrum data of Iodoarene derivative A are as described below.

$^1$H NMR (CDCl$_3$, 400 MHz) δ 1.33 (d, J=6.4 Hz, 6H), 1.40-1.60 (brs, 4H), 2.91-2.99 (m, 4H), 4.37-4.44 (m, 2H), 6.50 (d, J=8.4 Hz, 2H), 7.20 (t, J=8.4 Hz, 1H); $^{13}$C NMR (CDCl$_3$, 100 MHz) δ 17.2 (2C), 47.5 (2C), 82.1, 106.7 (2C), 129.5, 158.2 (2C).

Synthesis of Iodoarene Derivative C

Benzoyl chloride (0.3 mL, 2.79 mmol) was added to a solution, in which Iodoarene derivative A (326 mg, 0.93 mmol) was dissolved into CH$_2$Cl$_2$ (8.0 mL) and pyridine (1.5 mL), at 0° C. and agitation was performed at room temperature for a night. The resulting reaction mixed solution was poured into 1-N HCl, and extraction was performed with CHCl$_3$. An organic layer was washed with a saturated NaHCO$_3$ aqueous solution, and was dried with anhydrous MgSO$_4$. The solvent was removed by distillation in a vacuum. The residue was refined by silica gel flash column chromatography (dissolution medium hexane-EtOAc=4:1 (v/v)) to obtain Iodoarene derivative C (0.11 g, 0.20 mmol) at a yield of 23%. The spectrum data of Iodoarene derivative C are as described below.

$^1$H NMR (CDCl$_3$, 400 MHz) δ 1.42 (d, J=6.0 Hz, 6H), 3.61-3.68 (m, 2H), 3.93 (ddd, J=3.6, 6.4, 14.4 Hz, 2H), 4.61-4.70 (m, 2H), 6.53 (d, J=8.4 Hz, 2H), 6.80-6.90 (m, 2H), 7.22 (t, J=8.4 Hz, 1H), 7.42 (t, J=7.6 Hz, 4H), 7.50 (t, J=7.6 Hz, 2H), 7.80 (d, J=7.6 Hz, 4H); $^{13}$C NMR (CDCl$_3$, 100 MHz) δ 17.4 (2C), 44.6 (2C), 75.2 (2C), 81.9, 107.3 (2C), 127.0 (4C), 128.5 (4C), 130.2, 131.5 (2C), 134.1 (2C), 157.7 (2C), 167.5 (2C).

Synthesis of Iodoarene Derivative D

Synthesis was performed as with Iodoarene derivative C except that 4-(trifluoromethyl)benzoyl chloride was used instead of benzoyl chloride. The yield was 26%. The spectrum data of Iodoarene derivative D are as described below.

$^1$H NMR (CDCl$_3$, 400 MHz) δ 1.41 (d, J=6.4 Hz, 6H), 3.61-3.68 (m, 2H), 3.92 (ddd, J=3.2, 6.4, 14.0 Hz, 2H), 4.64-4.71 (m, 2H), 6.54 (d, J=8.4 Hz, 2H), 6.98-7.10 (m, 2H), 7.22 (t, J=8.4 Hz, 1H), 7.66 (d, J=8.4 Hz, 4H), 7.90 (d, J=8.4 Hz, 4H); $^{13}$C NMR (CDCl$_3$, 100 MHz) δ 17.4 (2C), 44.7 (2C), 75.0 (2C), 81.7, 107.3 (2C), 123.5 (d, $J_{C-F}$=272 Hz, 2C), 125.6 (d, $J_{C-F}$=3 Hz, 4C), 127.5 (4C), 130.3, 133.2 (q, $J_{C-F}$=32 Hz, 2C), 137.3 (2C), 157.6 (2C), 166.3 (2C); $^{19}$F NMR (CDCl$_3$, 376 MHz) δ -62.9.

Synthesis Of Iodoarene Derivative E

Synthesis was performed as with Iodoarene derivative C except that 4-methoxybenzoyl chloride was used instead of benzoyl chloride. The yield was 22%. The spectrum data of Iodoarene derivative E are as described below.

$^1$H NMR (CDCl$_3$, 400 MHz) δ 1.40 (d, J=6.0 Hz, 6H), 3.59-3.65 (m, 2H), 3.83 (s, 6H), 3.89 (ddd, J=3.2, 6.4, 13.6 Hz, 2H), 4.61-4.68 (m, 2H), 6.53 (d, J=8.0 Hz, 2H), 6.80-6.89 (m, 2H), 6.90 (d, J=8.4 Hz, 4H), 7.20 (t, J=8.0 Hz, 1H), 7.79 (d, J=8.4 Hz, 4H); $^{13}$C NMR (CDCl$_3$, 100 MHz) δ 17.4 (2C), 44.5 (2C), 55.4 (2C), 75.2 (2C), 81.8, 107.2 (2C), 113.7 (4C), 126.3 (2C), 128.8 (4C), 130.2, 157.7 (2C), 162.2 (2C), 167.0 (2C).

Synthesis of Iodoarene Derivative F

Synthesis was performed as with Iodoarene derivative C except that 3,5-bis(trifluoromethyl)benzoyl chloride was used instead of benzoyl chloride. The yield was 39%. The spectrum data of Iodoarene derivative F are as described below.

¹H NMR (CDCl₃, 400 MHz) δ 1.42 (d, J=6.0 Hz, 6H), 3.69-3.75 (m, 2H), 3.93 (ddd, J=3.6, 6.0, 13.2 Hz, 2H), 4.66-4.74 (m, 2H), 6.56 (d, J=8.4 Hz, 2H), 6.98-7.08 (m, 2H), 7.25 (t, J=8.4 Hz, 1H), 8.00 (s, 2H), 8.29 (s, 4H); ¹³C NMR (CDCl₃, 100 MHz) δ 17.3 (2C), 44.8 (2C), 74.7 (2C), 81.5, 107.4 (2C), 123.0 (d, $J_{C-F}$=271 Hz, 4C), 125.1 (2C), 127.4 (4C), 130.4, 132.1 (q, $J_{C-F}$=35 Hz, 4C), 136.1 (2C), 157.4 (2C), 164.6 (2C); ¹⁹F NMR (CDCl₃, 376 MHz) δ −62.9.

Synthesis of Iodoarene Derivative G

Synthesis was performed as with Iodoarene derivative C except that 3,5-dimethoxybenzoyl chloride was used instead of benzoyl chloride. The yield was 49%. The spectrum data of Iodoarene derivative G are as described below.

¹H NMR (CDCl₃, 400 MHz) δ 1.40 (d, J=6.0 Hz, 6H), 3.60-3.66 (m, 2H), 3.80 (s, 12H), 3.89 (ddd, J=3.2, 6.4, 13.6 Hz, 2H), 4.61-4.69 (m, 2H), 6.53 (d, J=8.0 Hz, 2H), 6.56 (t, J=2.4 Hz, 2H), 6.79-6.83 (m, 2H), 6.92 (d, J=2.4 Hz, 4H), 7.22 (t, J=8.0 Hz, 1H); ¹³C NMR (CDCl₃, 100 MHz) δ 17.4 (2C), 44.6 (2C), 55.6 (4C), 75.1 (2C), 81.8, 103.9 (2C), 104.7 (4C), 107.2 (2C), 113.7 (4C), 130.2, 136.3 (2C), 157.6 (2C), 160.8 (4C), 167.3 (2C).

Synthesis of Iodoarene Derivative I

Synthesis was performed as with Iodoarene derivative C except that 2,4,6-trimethylbenzoyl chloride was used instead of benzoyl chloride. The yield was 65%. The spectrum data of Iodoarene derivative I are as described below.

¹H NMR (CDCl₃, 400 MHz) δ 1.40 (d, J=6.4 Hz, 6H), 2.20 (s, 12H), 2.25 (s, 6H), 3.52-3.58 (m, 2H), 3.89 (ddd, J=3.2, 6.8, 14.0 Hz, 2H), 4.65-4.69 (m, 2H), 6.25-6.28 (m, 2H), 6.52 (d, J=8.4 Hz, 2H), 7.22 (t, J=8.4 Hz, 1H); ¹³C NMR (CDCl₃, 100 MHz) δ 17.4 (2C), 19.1 (4C), 21.0 (2C), 44.4 (2C), 74.9 (2C), 82.1, 107.1 (2C), 128.1 (4C), 130.0, 134.0 (4C), 134.6 (2C), 138.3 (2C), 157.5 (2C), 170.8 (2C).

Synthesis of Iodoarene Derivative K

Synthesis was performed as with Iodoarene derivative C except that 1-naphthoyl chloride was used instead of benzoyl chloride. The yield was 56%. The spectrum data of Iodoarene derivative K are as described below.

¹H NMR (CDCl₃, 400 MHz) δ 1.44 (d, J=6.0 Hz, 6H), 3.65-3.72 (m, 2H), 3.97 (ddd, J=3.2, 6.4, 13.6 Hz, 2H), 4.71-4.76 (m, 2H), 6.57 (d, J=8.0 Hz, 2H), 6.66-6.72 (m, 2H), 7.24 (t, J=8.0 Hz, 1H), 7.40 (t, J=7.6 Hz, 2H), 7.45-7.51 (m, 4H), 7.58 (d, J=7.6 Hz, 2H), 7.85 (d, J=9.2 Hz, 2H), 7.89 (d, J=7.6 Hz, 2H), 8.28 (d, J=7.6 Hz, 2H); ¹³C NMR (CDCl₃, 100 MHz) δ 17.5 (2C), 44.7 (2C), 75.2 (2C), 82.2, 107.4 (2C), 124.6 (2C), 125.1 (2C), 125.4 (2C), 126.4 (2C), 127.1 (2C), 128.3 (2C), 130.0, 130.1 (2C), 130.7 (2C), 133.6 (2C), 134.1 (2C), 157.7 (2C), 170.0 (2C).

Synthesis of Iodoarene Derivative L

Synthesis was performed as with Iodoarene derivative C except that 2-naphthoyl chloride was used instead of benzoyl chloride. The yield was 62%. The spectrum data of Iodoarene derivative L are as described below.

¹H NMR (CDCl₃, 400 MHz) δ 1.40 (d, J=6.0 Hz, 6H), 3.65-3.71 (m, 2H), 3.93 (ddd, J=3.6, 6.4, 13.6 Hz, 2H), 4.63-4.70 (m, 2H), 6.52 (d, J=8.4 Hz, 2H), 7.12-7.16 (m, 2H), 7.17 (t, J=8.4 Hz, 1H), 7.44-7.53 (m, 4H), 7.80-7.93 (m, 8H), 8.33 (s, 2H); ¹³C NMR (CDCl₃, 100 MHz) δ 17.4 (2C), 44.6 (2C), 75.0 (2C), 81.8, 107.2 (2C), 123.6 (2C), 126.6 (2C), 127.5 (2C), 127.6 (4C), 128.3 (2C), 128.8 (2C), 130.1 (2C), 131.2 (2C), 132.4 (2C), 134.2 (2C), 157.6 (2C), 167.5 (2C).

Synthesis of Iodoarene Derivative M

Synthesis was performed as with Iodoarene derivative C except that 9-anthracenecarbonyl chloride was used instead of benzoyl chloride. The yield was 73%. The spectrum data of Iodoarene derivative M are as described below.

¹H NMR (CDCl₃, 400 MHz) δ 1.48 (d, J=6.0 Hz, 6H), 3.65-3.72 (m, 2H), 4.19 (ddd, J=3.2, 6.8, 13.6 Hz, 2H), 4.84-4.88 (m, 2H), 6.63-6.69 (m, 2H), 6.65 (d, J=8.4 Hz, 2H), 7.32 (t, J=8.4 Hz, 1H), 7.08-8.18 (m, 16H), 8.44 (s, 2H); ¹³C NMR (CDCl₃, 100 MHz) δ 17.7 (2C), 45.0 (2C), 75.0 (2C), 82.4, 107.2 (2C), 124.9 (4C), 125.3 (4C), 126.5 (4C), 127.9 (2C), 128.3 (4C), 128.4 (4C), 130.0, 130.9 (4C), 131.4 (4C), 157.7 (2C), 169.7 (2C).

Synthesis of Iodoarene Derivative H

A solution was prepared by dissolving 2,6-diethylbenzoic acid (0.64 g, 3.57 mmol), EDAC.HCL (0.82 g, 4.27 mmol), and i-PrNEt (0.97 mL, 4.27 mmol) into THF (7.4 mL), and HOBt (0.58 g, 4.27 mmol) was added. After agitation was performed at room temperature for 10 minutes, a solution in which Iodoarene derivative A (0.31 g, 0.89 mmol) was dissolved into THF (5.9 mL) was added to the reaction mixed solution at room temperature, and reflux was performed for a night. The resulting mixed solution was cooled to room temperature and was poured into 1-N HCl. Extraction was performed with EtOAc. An organic layer was washed with a saturated NaHCO₃ aqueous solution, and was dried with anhydrous MgSO₄. After the solvent was removed, the residue was refined by silica gel flash column chromatography (dissolution medium hexane-EtOAc=1:1 (v/v)) to obtain Iodoarene derivative H (0.10 g, 0.15 mmol) at a yield of 17%. The spectrum data of Iodoarene derivative H are as described below.

¹H NMR (CDCl₃, 400 MHz) δ 1.10 (t, J=7.2 Hz, 12H), 1.39 (d, J=6.0 Hz, 6H), 2.25 (q, J=7.2 Hz, 8H), 3.48-3.54 (m, 2H), 3.96 (ddd, J=3.2, 6.8, 14.0 Hz, 2H), 4.67-4.72 (m, 2H), 6.26-6.28 (m, 2H), 6.53 (d, J=8.4 Hz, 2H), 7.03 (d, J=7.8 Hz, 4H), 7.21-7.26 (m, 3H); ¹³C NMR (CDCl₃, 100 MHz) δ 15.6 (4C), 17.3 (2C), 26.2 (2C), 44.6 (2C), 74.7 (2C), 82.0, 106.8 (2C), 125.7 (4C), 129.0 (2C), 130.0, 136.3 (2C), 140.2 (4C), 157.6 (2C), 170.5 (2C).

Synthesis of Iodoarene Derivative J

A solution in which Iodoarene derivative A (0.29 g, 0.83 mmol) was dissolved into THF (6 mL) was added to a suspension in which NaH (60% oil suspension, 0.10 g, 2.5 mmol) was dispersed into THE (4.1 mL) at 0° C. After agitation was performed for 2 hours, a solution in which 2,4,6-triisopropylbenzoyl chloride (1.10 g, 4.13 mmol) was dissolved into THF (10 mL) and DMAP (0.1 g, 0.83 mmol) was added to the reaction mixed solution. After agitation was performed at room temperature for 2 hours, the resulting mixed solution was poured into water at 0° C., and extraction was performed with EtOAc. After an organic layer was dried with anhydrous MgSO₄, the solvent was removed by distillation in a vacuum. The residue was refined by silica gel flash column chromatography (dissolution medium hexane-EtOAc=2:1 (v/v)) to obtain Iodoarene derivative J (0.10 g, 0.15 mmol) at a yield of 45%. The spectrum data of Iodoarene derivative J are as described below.

¹H NMR (CDCl₃, 400 MHz) δ 0.89 (d, J=6.0 Hz, 4H), 1.12 (d, J=8.7 Hz, 4H), 1.18-1.30 (m, 22H), 1.37 (d, J=6.0 Hz, 6H), 2.70-2.85 (m, 2H), 2.85 (septet, J=7.2 Hz, 2H), 2.93-3.02 (m, 2H), 3.44-3.50 (m, 2H), 4.01 (ddd, J=2.4, 6.8, 14.0 Hz, 2H), 4.71-4.74 (m, 2H), 6.29-6.33 (m, 2H), 6.52 (d, J=8.4 Hz, 2H), 6.92 (s, 2H), 6.99 (s, 2H), 7.24 (t, J=8.4 Hz, 1H); $^{13}$C NMR (CDCl$_3$, 100 MHz) δ 17.2 (2C), 23.9 (8C), 24.2 (2C), 24.6 (2C), 30.9 (2C), 31.3 (2C), 34.3 (2C), 44.8 (2C), 74.4 (2C), 81.9, 106.4 (2C), 120.9 (4C), 129.9, 133.0 (2C), 144.7 (2C), 149.7 (4C), 157.6 (2C), 171.2 (2C).

Synthesis of Iodoarene Derivative R

Synthesis was performed as with Iodoarene derivative M except that 2-iodo-5-methylbenzene-1,3-diol was used instead of 2-iodoresorcinol. The yield was 5%. The spectrum data of Iodoarene derivative R are as described below.

$^1$H NMR (CDCl$_3$, 400 MHz) δ 1.46 (d, J=6.0 Hz, 6H), 2.39 (s, 3H), 3.66 (ddd, J=5.6, 7.6, 14.0 Hz, 2H), 4.18 (ddd, J=3.2, 7.2, 14.0 Hz, 2H), 4.80-4.88 (m, 2H), 6.48 (s, 2H), 6.62-6.65 (m, 2H), 7.05-8.23 (m, 16H), 8.44 (s, 2H); $^{13}$C NMR (CDCl$_3$, 100 MHz) δ 17.8 (2C), 21.9, 45.1 (2C), 75.1 (2C), 78.6, 108.4 (2C), 125.0 (4C), 125.4 (4C), 126.5 (4C), 127.9 (2C), 128.3 (4C), 128.4 (4C), 131.0 (4C), 131.4 (4C), 140.6, 157.5 (2C), 169.8 (2C).

Synthesis of Iodoarene Derivative S

Synthesis was performed as with Iodoarene derivative I except that 2-iodophenol was used instead of 2-iodoresorcinol. The yield was 79% (3 steps). The spectrum data of Iodoarene derivative S are as described below.

$^1$H NMR (CDCl$_3$, 400 MHz) δ 1.41 (d, J=6.4 Hz, 3H), 2.22 (s, 6H), 2.26 (s, 3H), 3.55 (ddd, J=5.5, 7.3, 13.8 Hz, 1H), 3.95 (ddd, J=3.2, 6.4, 13.8 Hz, 1H), 4.65-4.72 (m, 1H), 6.20-6.30 (m, 1H), 6.72 (dt, J=1.4, 8.2 Hz, 1H), 6.86 (dd, J=1.4, 8.2 Hz, 1H), 7.29 (dt, J=1.4, 8.2 Hz, 1H), 7.75 (dd, J=1.4, 8.2 Hz, 1H); $^{13}$C NMR (CDCl$_3$, 100 MHz) δ 17.3, 19.1 (2C), 21.1, 44.5, 74.8, 88.1, 113.8, 123.1, 128.2 (2C), 129.6, 134.0 (2C), 134.6, 138.4, 139.5, 156.0, 170.8

6.80 (s, 2H), 7.13 (d, J=2.0 Hz, 1H); $^{13}$C NMR (CDCl$_3$, 100 MHz) δ 17.5, 19.1 (2C), 21.1, 30.1 (3C), 31.2 (3C), 34.9, 37.7, 44.5, 75.3, 88.1, 109.2, 118.4, 128.1 (2C), 134.0 (2C), 134.7, 138.3, 151.6, 152.0, 155.6, 170.9

Synthesis of Iodoarene Derivative U

Synthesis was performed as with Iodoarene derivative C except that 2,4,6-trimethylbenzenesulfonyl chloride was used instead of benzoyl chloride, while a reaction formula described below was followed. The yield was 70%. The spectrum data of Iodoarene derivative U are as described below.

$^1$H NMR (CDCl$_3$, 400 MHz) δ 1.27 (d, J=6.4 Hz, 6H), 2.28 (s, 6H), 2.63 (s, 12H), 3.06-3.12 (m, 2H), 3.23-3.29 (m, 2H), 4.38-4.47 (m, 2H), 5.28-5.35 (m, 2H), 6.31 (d, J=8.2 Hz, 2H), 6.91 (s, 4H), 7.10 (t, J=8.2 Hz, 1H); $^{13}$C NMR (CDCl$_3$, 100 MHz) δ 17.0 (2C), 20.7 (2C), 22.9 (4C), 47.4 (2C), 74.0 (2C), 81.7, 106.8 (2C), 129.6, 131.8 (4C), 133.6 (2C), 138.5 (4C), 142.0 (2C), 156.9 (2C).

Synthesis of Iodoarene Derivative V

The reaction formula described below was followed. A solution in which Iodobenzene derivative A (0.11 g, 0.32 mmol), benzene hexafluoride (0.18 mL, 1.6 mmol), and triethylamine (0.16 mL, 1.6 mmol) were dissolved into DMF (1 mL) was agitated at 100° C. After 2 days were elapsed, the solvent was removed by distillation under reduced pressure. A crude product was refined by silica gel flash column chromatography (dissolution medium hexane-EtOAc=10:1 (v/v)) to obtain Iodoarene derivative V (43.7 mg, 0.064 mmol) at a yield of 20%. The spectrum data of Iodoarene derivative V are as described below.

$^1$H NMR (CDCl$_3$, 400 MHz) δ 1.41 (d, J=6.0 Hz, 6H), 3.49-3.56 (m, 2H), 3.64-3.70 (m, 2H), 4.22-4.36 (m, 2H), 4.57-4.63 (m, 2H), 6.46 (d, J=8.2 Hz, 2H), 7.19 (t, J=8.2 Hz, 1H); $^{19}$F NMR (CDCl$_3$, 376 MHz) δ −171.3 (s, 2F), −164.2 (t, J=23 Hz, 4F), −158.6 (d, J=23 Hz, 4F).

[Chem. 4]

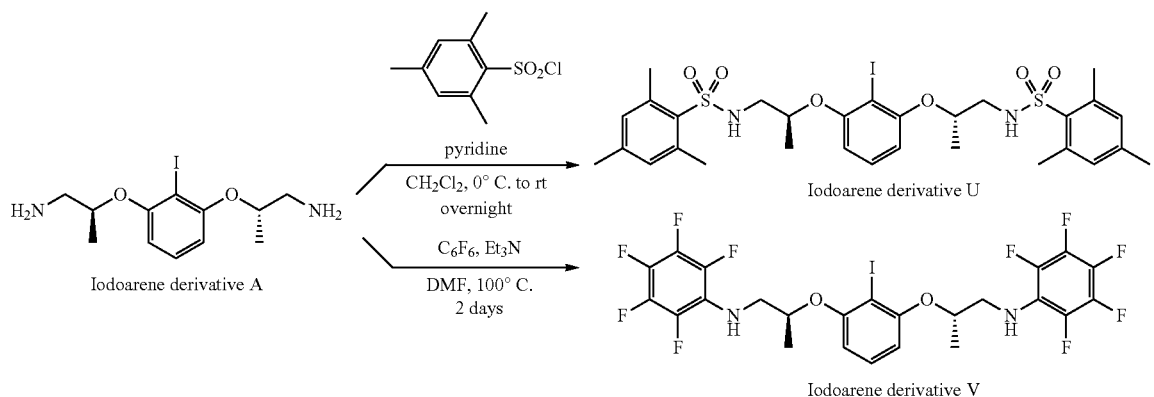

Synthesis of Iodoarene Derivative T

Synthesis was performed as with Iodoarene derivative I except that 3,5-di-tert-butyl-2-iodophenol was used instead of 2-iodoresorcinol. The yield was 51% (3 steps). The spectrum data of Iodoarene derivative T are as described below.

$^1$H NMR (CDCl$_3$, 400 MHz) δ 1.31 (s, 9H), 1.43 (d, J=6.4 Hz, 3H), 1.55 (s, 9H), 2.21 (s, 6H), 2.25 (s, 3H), 3.61 (ddd, J=5.6, 6.8, 14.0 Hz, 1H), 3.94 (ddd, J=3.2, 6.4, 14.0 Hz, 1H), 4.65-4.72 (m, 1H), 6.40-6.42 (m, 1H), 6.76 (d, J=2.0 Hz, 1H),

[1-2] Synthesis of Iodoarene Derivative Type 2

Iodoarene derivatives N to Q were synthesized following the reaction formulae described below. They were referred to as Type 2, in which a substituent was bonded to the carbon atom on the nitrogen side in the ethylene chain between the oxygen atom and the nitrogen atom in the side chain. All the iodoarene derivatives N to Q correspond to the examples according to the present invention.

[Chem. 5]

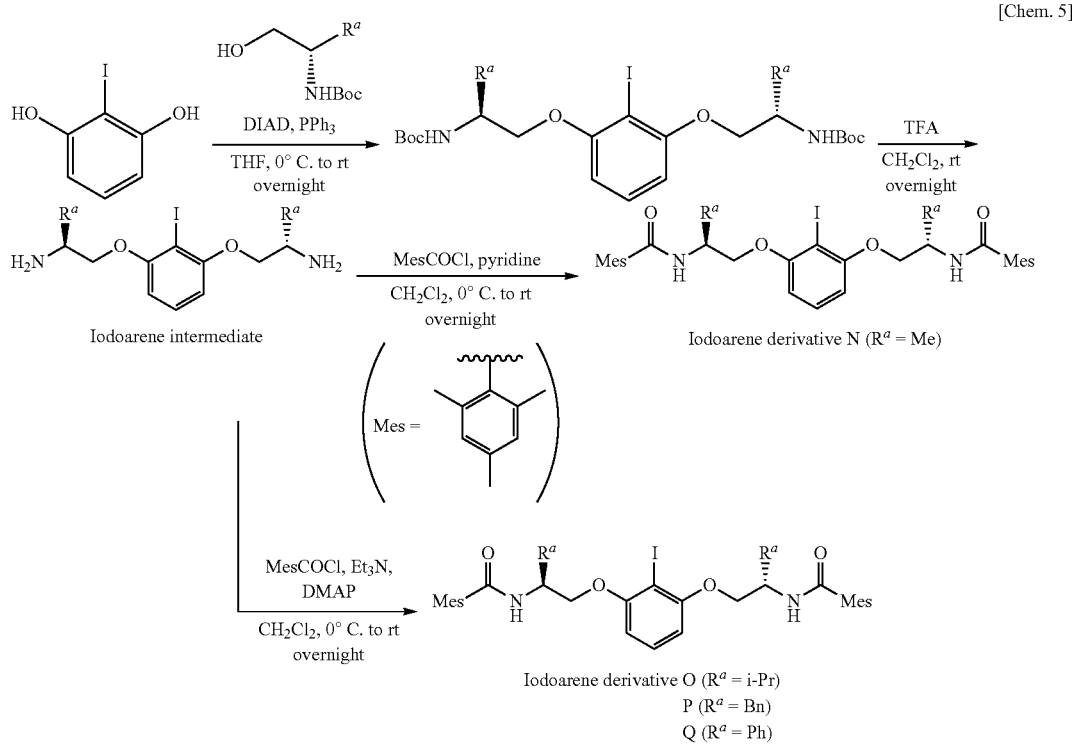

Synthesis of Iodoarene Derivative N

Iodoarene derivative N was synthesized following the above-described reaction formula in conformity with the synthesis of Iodoarene derivative I. The yield from an iodoarene intermediate was 14%. The spectrum data thereof are as described below.

$^1$H NMR (CDCl$_3$, 400 MHz) δ 1.48 (d, J=6.8 Hz, 6H), 2.26 (s, 18H), 4.07 (dd, J=2.8, 9.2 Hz, 2H), 4.20 (dd, J=3.6, 9.2 Hz, 2H), 4.59-4.67 (m, 2H), 6.14 (d, J=8.4 Hz, 2H), 6.50 (d, J=8.4 Hz, 2H), 6.82 (s, 4H), 7.25 (t, J=8.4 Hz, 1H); $^{13}$C NMR (CDCl$_3$, 100 MHz) δ 17.7 (2C), 19.1 (4C), 21.1 (2C), 44.8 (2C), 71.7 (2C), 78.6, 105.4 (2C), 128.2 (4C), 130.1, 134.1 (4C), 134.5 (2C), 138.5 (2C), 158.2 (2C), 170.1 (2C).

Synthesis of Iodoarene Derivative O

Iodoarene derivative O was synthesized following the above-described reaction formula. In a final step, 2,4,6-trimethylbenzoyl chloride (0.73 mL, 4.39 mmol) was added at 0° C. to a solution in which an iodoarene intermediate (0.59 g, 1.46 mmol), DMAP (0.18 g, 1.46 mmol), and Et$_3$N (0.48 mL, 4.39 mmol) were dissolved into CH$_2$Cl$_2$ (10.4 mL), and agitation was performed at room temperature for a night. The resulting reaction mixed solution was poured into 1-N HCl, and extraction was performed with CHCl$_3$. An organic layer was washed with a saturated NaHCO$_3$ aqueous solution and a saline solution, and was dried with anhydrous MgSO$_4$. The solvent was removed by distillation in a vacuum. The residue was refined by silica gel flash column chromatography (dissolution medium hexane-EtOAc=2:1 (v/v)) to obtain Iodoarene derivative O (0.55 g, 0.79 mmol) at a yield of 54%. The spectrum data of Iodoarene derivative C are as described below.

$^1$H NMR (CDCl$_3$, 400 MHz) δ 1.06 (d, J=6.8 Hz, 6H), 1.11 (d, J=6.8 Hz, 6H), 2.24 (s, 12H), 2.26 (s, 6H), 4.16-4.28 (m, 6H), 6.12 (d, J=8.4 Hz, 2H), 6.51 (d, J=8.0 Hz, 2H), 6.82 (s, 4H), 7.25 (t, J=8.0 Hz, 1H); $^{13}$C NMR (CDCl$_3$, 100 MHz) δ 19.2 (4C), 19.7 (4C), 21.0 (2C), 29.1 (2C), 54.4 (2C), 68.9 (2C), 78.5, 105.2 (2C), 128.2 (4C), 130.0, 134.0 (4C), 134.8 (2C), 138.3 (2C), 158.2 (2C), 170.3 (2C).

Synthesis of Iodoarene Derivative P

Iodoarene derivative P was synthesized following the above-described reaction formula in conformity with the synthesis of Iodoarene derivative O. The yield from an Iodoarene intermediate was 40%. The spectrum data thereof are as described below.

$^1$H NMR (CDCl$_3$, 400 MHz) δ 2.14 (s, 12H), 2.25 (s, 6H), 3.18-3.27 (m, 4H), 4.05 (dd, J=2.0, 9.2 Hz, 2H), 4.18 (dd, J=3.6, 9.2 Hz, 2H), 4.75-4.80 (m, 2H), 6.14 (d, J=8.4 Hz, 2H), 6.45 (d, J=8.0 Hz, 2H), 6.81 (s, 4H), 7.19-7.30 (m, 11H); $^{13}$C NMR (CDCl$_3$, 100 MHz) δ 18.9 (4C), 21.1 (2C), 37.4 (2C), 50.2 (2C), 69.2 (2C), 78.5, 105.5 (2C), 126.8 (2C), 128.2 (4C), 128.4 (2C), 128.7 (4C), 130.3, 134.2 (4C), 134.5 (2C), 137.5 (2C), 138.5 (2C), 158.0 (2C), 170.2 (2C).

Synthesis of Iodoarene Derivative Q

Iodoarene derivative Q was synthesized following the above-described reaction formula in conformity with the synthesis of Iodoarene derivative O. The yield from an iodoarene intermediate was 74%. The spectrum data thereof are as described below.

$^1$H NMR (CDCl$_3$, 400 MHz) δ 2.22 (s, 12H), 2.26 (s, 6H), 4.34-4.40 (m, 4H), 5.61-5.65 (m, 2H), 6.46 (d, J=8.0 Hz, 2H), 6.69 (d, J=8.0 Hz, 2H), 6.81 (s, 4H), 7.19 (t, J=8.0 Hz, 1H), 7.29-7.38 (m, 6H), 7.55 (d, J=7.2 Hz, 4H); $^{13}$C NMR (CDCl$_3$, 100 MHz) δ 19.3 (4C), 21.1 (2C), 52.5 (2C), 71.5 (2C), 78.7, 105.7 (2C), 127.5 (4C), 127.9 (2C), 128.2 (4C), 128.6 (4C), 130.1, 134.2 (4C), 134.4 (2C), 138.5 (2C), 138.9 (2C), 158.1 (2C), 170.1 (2C).

[2] Synthesis of Optically Active Spirolactone Compound by Oxidation of 1-Naphthol Compound

[2-1] Synthesis of 1-Naphthol Compound S1 (Refer to the Formula Described Below)

Pivalic acid (1.53 g, 15 mmol) was added to a solution in which 1-naphthol (4.33 g, 30 mmol) and triethylorthoacrylate (6.0 mL, 48 mmol) were dissolved into toluene (100 mL), while the solution was agitated. The resulting mixed solution was refluxed for a day. The resulting mixed solution was poured into 1-N NaOH (30 mL). Extraction with Et$_2$O was performed two times and washing was performed with a saline solution. Organic layers were mixed and dried with anhydrous Na$_2$SO$_4$. The solvent was removed by distillation in a vacuum. The residue was refined by silica gel flash chromatography (dissolution medium hexane-EtOAc=15:1 (v/v)) to obtain a pyran derivative (8.17 g, 30 mL, yield more than 99%) which was colorless oil. A solution in which the resulting pyran derivative (8.17 g, 30 mmol) was dissolved into Et$_2$O (80 mL) was blended with 2-N HCl (40 mL) and the resulting reaction mixed solution was agitated at room temperature for a night. The resulting reaction mixed solution was subjected to extraction with EtOAc two times and washing was performed with a saline solution. Organic layers were mixed and dried with anhydrous Na$_2$SO$_4$. The solvent was removed by distillation in a vacuum. A solution in which the resulting crude product was dissolved into THF (30 mL) and MeOH (30 mL) was blended with 2-N NaOH (40 mL), and the resulting reaction mixed solution was agitated at room temperature for a night. The resulting reaction mixed solution was poured into 1-N HCl (100 mL), extraction with EtOAc was performed two times, and washing was performed with a saline solution. Organic layers were mixed and dried with anhydrous MgSO$_4$. The solvent was removed by distillation in a vacuum. The residue was refined by silica gel flash chromatography (dissolution medium hexane-EtOAc=4:1 to 2:1 (v/v)) to obtain Naphthol compound S1, that is, 3-(1-hydroxynaphthalen-2-yl)propanoic acid (4.05 g, 18.7 mmol) at a yield of 62%. The spectrum data thereof are as described below. In this regard, various naphthol compounds used as reaction substrates in Examples 41 to 50 described later were synthesized by this method.

Naphthol compound S1: $^1$H NMR (CDCl$_3$, 400 MHz) δ 2.86-2.89 (m, 2H), 3.02-3.06 (m, 2H), 7.17 (d, J=8.4 Hz, 1H), 7.39 (d, J=8.4 Hz, 1H), 7.40-7.47 (m, 2H), 7.65 (brs, 1H), 7.73-7.76 (m, 1H), 8.24-8.27 (m, 1H); $^{13}$C NMR (CDCl$_3$, 100 MHz) δ 24.1, 34.7, 120.0, 120.7, 122.1, 125.3, 125.7, 125.9, 127.3, 128.1, 133.7, 149.2, 180.5.

[Chem. 6]

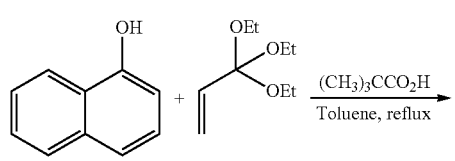

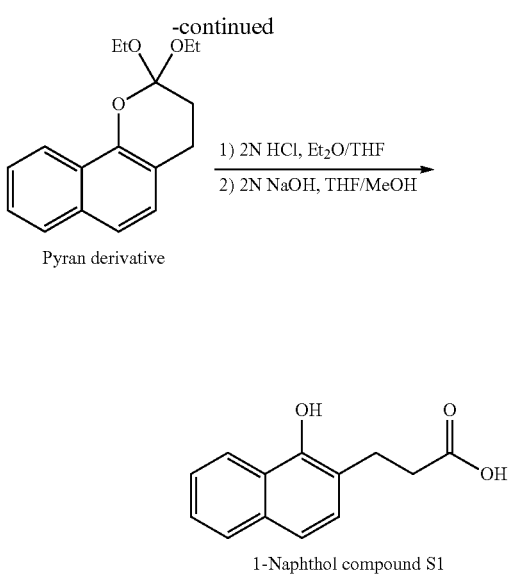

Pyran derivative

1-Naphthol compound S1

[2-2] Synthesis Examples by Using Various Catalyst Precursors

As indicated by Examples 1 to 22 shown in Table 1 and Table 2, Spirolactone compound P1 was obtained by reacting Naphthol compound S1 with various Iodoarene derivatives A to V and m-CPBA. The synthesis procedure of Example 9 will be described below as a typical example.

In Example 9, initially, a solution in which 1-Naphthol compound S1 (21.6 mg, 0.11 mmol), Iodoarene derivative I (6.4 mg, 0.01 mmol, 10 percent by mole), and mCPBA (26.9 mg, 0.12 mmol, 1.2 equiv) were dissolved into chloroform (5 mL, S1 concentration 0.02 M) was agitated at 0° C. After 9 hours were elapsed, the reaction mixed solution was poured into a Na$_2$S$_2$O$_3$ aqueous solution (5 mL) and a NaHCO$_3$ aqueous solution (5 mL), and extraction with CHCl$_3$ was performed two times. An organic layer was dried with anhydrous MgSO$_4$. The solvent was removed by distillation in a vacuum. The residue was refined by silica gel flash chromatography (dissolution medium hexane-EtOAc=10:1.4:1 (v/v)) to obtain Spirolactone compound P1 (15.4 mg, 0.072 mmol) at a yield of 72% and 98% ee. The purity of mCPBA (produced by Aldrich) employed was 77% and the purity of chloroform (produced by Nacalai) employed was 99%. The spectrum data of Spirolactone compound P1 are as described below.

Spirolactone compound P1: $^1$H NMR (CDCl$_3$, 400 MHz) δ 2.18 (ddd, J=9.6, 11.0, 13.5 Hz, 1H), 2.49 (ddd, J=1.8, 9.6, 13.5 Hz, 1H), 2.60 (ddd, J=1.8, 9.6, 17.6 Hz, 1H), 2.92 (ddd, J=9.6, 11.0, 17.6 Hz, 1H), 6.21 (d, J=10.4 Hz, 1H), 6.66 (d, J=10.4 Hz, 1H), 7.26 (d, J=8.0 Hz, 1H), 7.41 (t, J=8.0 Hz, 1H), 7.62 (t, J=8.0 Hz, 1H), 8.02 (d, J=8.0 Hz, 1H); $^{13}$C NMR (CDCl$_3$, 100 MHz) δ 26.5, 31.2, 83.4, 127.3, 127.8, 127.9, 127.9, 129.0, 132.3, 135.7, 136.8, 176.5, 196.5; HPLC (OD-H column), Hexane-EtOH=10:1 as eluent, 1.0 mL/min, $t_R$=23.3 min, $t_S$=27.6 min.

TABLE 1
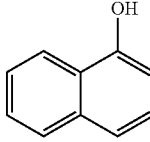
| | Catalyst precursor | | | Result | | |
|---|---|---|---|---|---|---|
| | Abbr. | Type | Structural formula | Yield (%) | ee (%) | Configuration |
| Example 1 | A | 1 | 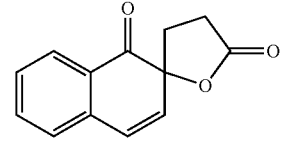 | 28 | 74 | S |
| Example 2 | B | 1 | 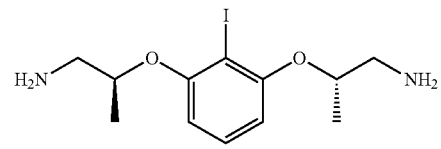 [SMILES: C[C@@H](CN)Oc1cccc(O[C@@H](C)CN)c1I] | 65 | 88 | S |
| Example 3 | C | 1 | 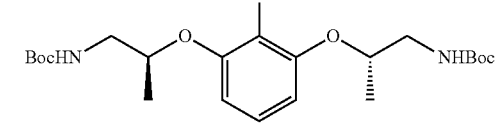 | 67 | 88 | S |
| Example 4 | D | 1 | 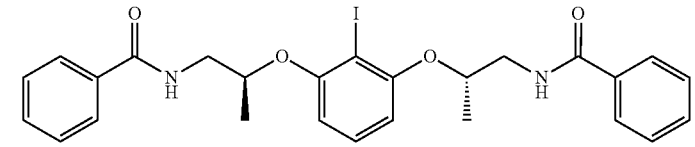 [SMILES: C[C@@H](CNC(=O)c1ccccc1)Oc1cccc(O[C@@H](C)CNC(=O)c2ccccc2)c1I] | 71 | 91 | S |
| Example 5 | E | 1 | 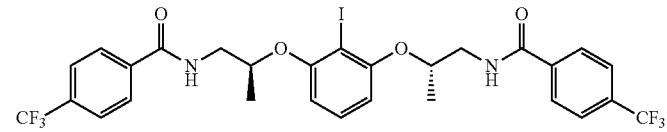 [SMILES: C[C@@H](CNC(=O)c1ccc(C(F)(F)F)cc1)Oc1cccc(O[C@@H](C)CNC(=O)c2ccc(C(F)(F)F)cc2)c1I] | 61 | 88 | S |
| Example 6 | F | 1 | 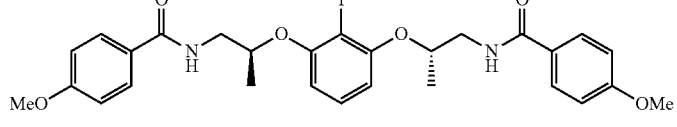 | 41 | 65 | S |
| Example 7 | G | 1 | 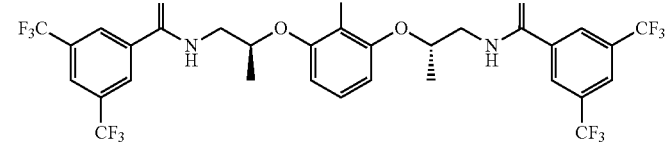 | 50 | 87 | S |
| Example 8 | H | 1 | 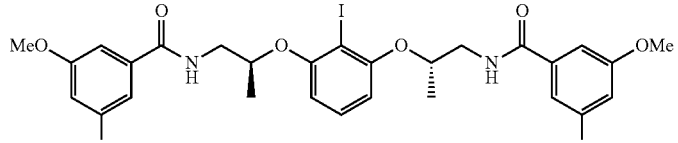 | 88 | 96 | S |

TABLE 1-continued 1-naphthol compound S1 + m-CPBA (1.2 equiv) → Spirolactone compound P1

Conditions: Catalyst precursor (10 mol %), CHCl$_3$ (0.02M), 0° C., 9 h

| | Catalyst presursor | | | Result | | |
|---|---|---|---|---|---|---|
| | Abbr. | Type | Structural formula | Yield (%) | ee (%) | Configuration |
| Example 9 | I | 1 | (mesityl amide derivative) | 72 | 98 | S |
| Example 10 | J | 1 | (2,4,6-triisopropylbenzamide derivative) | 90 | 88 | S |
| Example 11 | K | 1 | (1-naphthoyl amide derivative) | 69 | 94 | S |
| Example 12 | L | 1 | (2-naphthoyl amide derivative) | 54 | 90 | S |
| Example 13 | M | 1 | (9-anthracenyl amide derivative) | 83 | 97 | S |

TABLE 2

1-naphthol compound S1 + m-CPBA (1.2 equiv) → Spirolactone compound P1

Conditions: Catalyst precursor (10 mol %), CHCl$_3$ (0.02M), 0° C., 9 h

| | Catalyst presursor | | | Result | | |
|---|---|---|---|---|---|---|
| | Abbr. | Type | Structural formula | Yield (%) | ee (%) | Configuration |
| Example 14 | N | 2 | (mesityl amide derivative, R,R) | 52 | 90 | R |

TABLE 2-continued
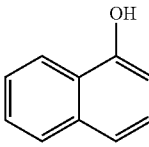
| | | | Catalyst presursor | Result | | |
|---|---|---|---|---|---|---|
| | Abbr. | Type | Structural formula | Yield (%) | ee (%) | Configuration |
| Example 15 | O | 2 | 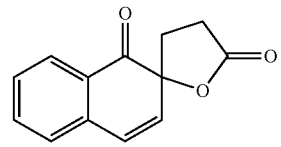 | 74 | 98 | R |
| Example 16 | P | 2 | 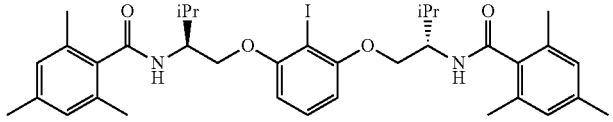 | 34 | 94 | R |
| Example 17 | Q | 2 | 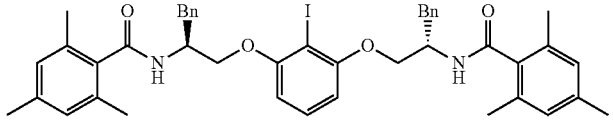 | 56 | 88 | R |
| Example 18 | R | 1 | 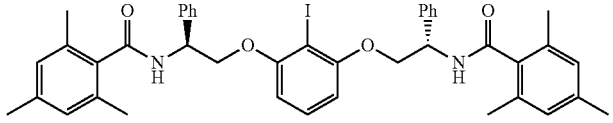 *1 | 84 | 95 | S |
| Example 19 | S | 1 | 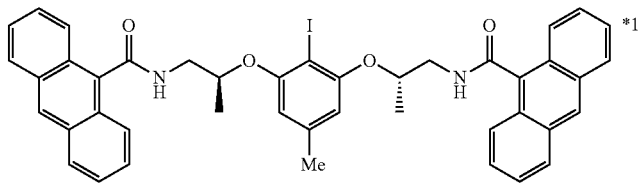 [SMILES: Cc1cc(O[C@@H](C)CNC(=O)c2c3ccccc3cc3ccccc23)c(I)c(O[C@@H](C)CNC(=O)c2c3ccccc3cc3ccccc23)c1] *2 | 58 | 70 | S |

TABLE 2-continued

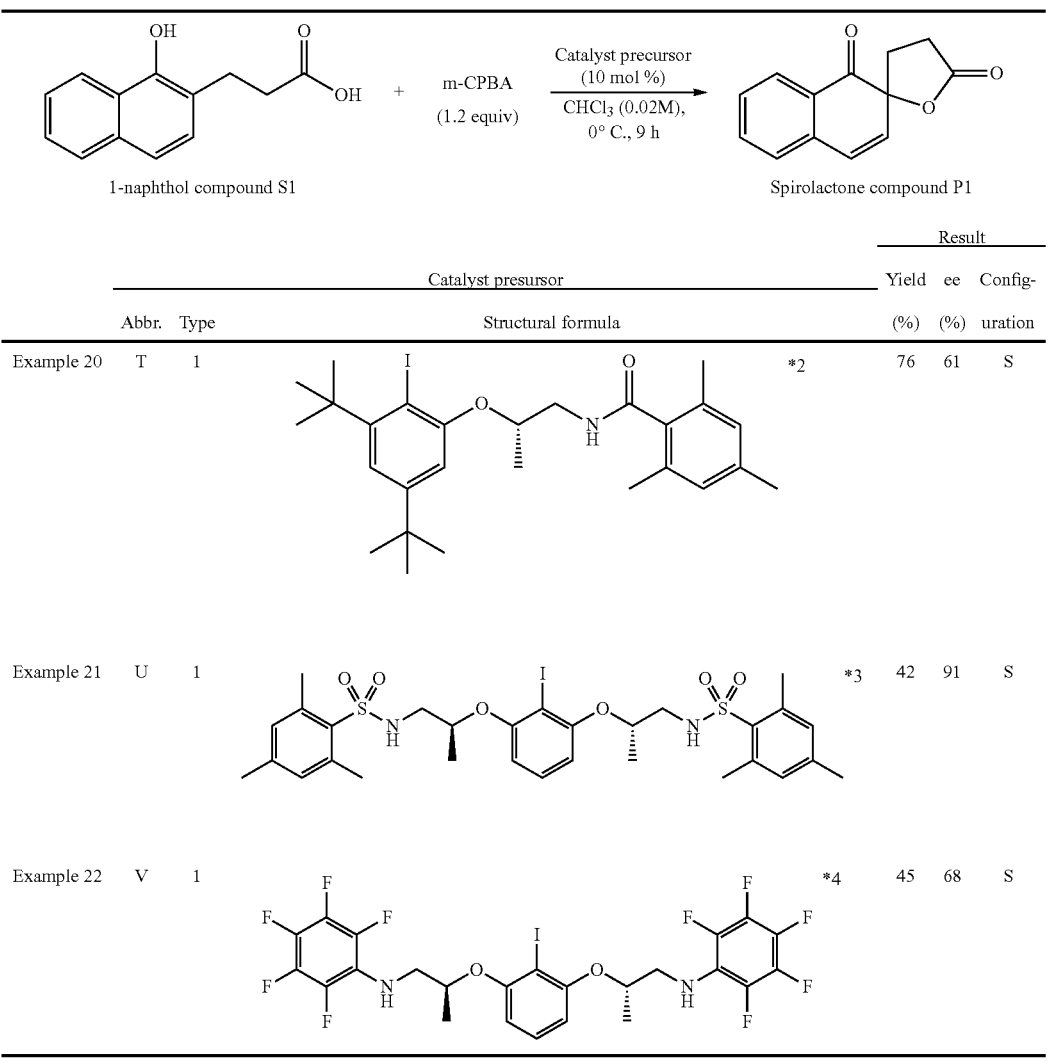

*1: The catalyst precursor was specified to be 5 percent by mole, and the reaction time was specified to be 18 h.
*2: The catalyst precursor was specified to be 5 percent by mole, mCPBA was specified to be a refined product, the solvent was specified to be DCE (0.02M) + EtOH (6 equiv), and the reaction time was specified to be 18 h.
*3: The reaction time was specified to be 19 h.
*4: The reaction time was specified to be 23 h.

As indicated by Examples 1 to 13 in Table 1 and Examples 21 and 22 in Table 2, when catalyst precursors of Type 1 were used, in the case where the terminal of the side chain of the catalyst precursor was —NH$_2$, the enantiomeric excess was high, but the yield was not sufficient (Example 1). On the other hand, in the case where the terminal of the side chain was —NHCO—, —NHSO$_2$—, or —NHAr—, the enantiomeric excess became still higher and the yield increased (Examples 2 to 13, 21, and 22). In particular, in the case where the terminal of the side chain was —NHC(=O)Ar and Ar was a mesityl group or a 9-anthracenyl group, as in Examples 9 and 13, the enantiomeric excess was very high.

As indicated by Examples 14 to 17 in Table 2, when the catalyst precursor of Type 2 was used, both the resulting enantiomeric excess and yield were good. In the case where the methyl group of —OCH$_2$CH(Me)NHC(=O)Ar serving as a side chain was changed to an isopropyl group, a benzyl group, or a phenyl group as well, the enantiomeric excess was a high value.

In Example 18 in Table 2, the catalyst precursor of Type 1 having a methyl group at the p position relative to the iodine atom of iodobenzene was used and both the enantiomeric excess and yield were very high as with Example 13 (not including a methyl group). In Example 19, the catalyst precursor of Type 1 in which iodobenzene had one side chain (that is, left-right asymmetry) was used. As a result, good results were obtained, although the enantiomeric excess and the yield decreased to some extent as compared with Example 9 (two side chains). In Example 20, the catalyst precursor of Type 1 having tert-butyl groups at the o position and the p position relative to the iodine atom of iodobenzene was used. As a result, good results were obtained, although the enantiomeric excess and the yield decreased to some extent as compared with Example 9.

[2-3] Examination of Reaction Condition

Synthesis of optically active spirolactone compound was performed in conformity with the reaction example by using Iodoarene derivative I in Example 9, where the reaction condition shown in Table 3 was adopted. The results thereof are shown in Table 3.

TABLE 3

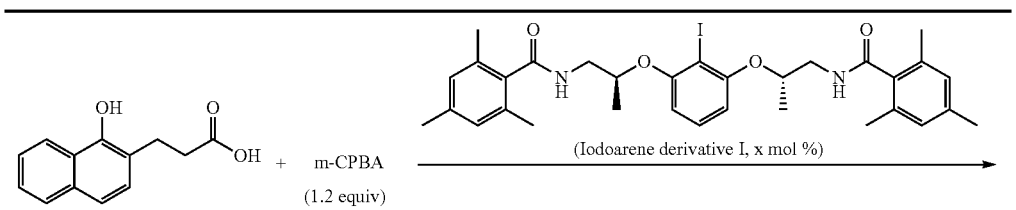

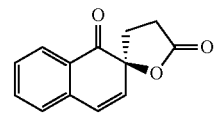

Spirolactone compound P1

| | x | m-CPBA | Solvent | Additive | Reaction condition | Yield (%) | ee(%) |
|---|---|---|---|---|---|---|---|
| Example 23 | 10 | Commercial product *1 | Commercial product | — | EtOAc(0.02M), 0° C., 26 h | 59 | 84 |
| Example 24 | 10 | Commercial product | Commercial product | — | $CH_3NO_2$(0.02M), 0° C., 18 h | 76 | 91 |
| Example 25 | 10 | Commercial product | Commercial product | — | $CHCl_3$(0.02M), 0° C., 9 h *3 | 72 | 98 |
| Example 26 | 5 | Refined product *2 | Refined product | — | $CHCl_3$(0.02M), 0° C., 18 h *4 | 47 | 90 |
| Example 27 | 5 | Refined product | Commercial product | — | DCE(0.02M), 0° C., 18 h *5 | 88 | 93 |
| Example 28 | 5 | Refined product | Commercial product | EtOH(1 eq) | DCE(0.02M), 0° C., 18 h | 81 | 93 |
| Example 29 | 5 | Refined product | Commercial product | EtOH(6 eq) | DCE(0.02M), 0° C., 18 h | 83 | 96 |
| Example 30 | 5 | Refined product | Commercial product | EtOH(34 eq) | DCE(0.02M), 0° C., 18 h | 71 | 97 |
| Example 31 | 5 | Refined product | Commercial product | MeOH(6 eq) | DCE(0.02M), 0° C., 18 h | 71 | 96 |
| Example 32 | 5 | Refined product | Commercial product | i-PrOH(6 eq) | DCE(0.02M), 0° C., 18 h | 70 | 94 |
| Example 33 | 5 | Refined product | Commercial product | t-BuOH(6 eq) | DCE(0.02M), 0° C., 18 h | 81 | 96 |
| Example 34 | 5 | Refined product | Commercial product | TFA(6 eq) | DCE(0.02M), 0° C., 18 h | 66 | 91 |
| Example 35 | 5 | Refined product | Commercial product | AcOH(6 eq) | DCE(0.02M), 0° C., 18 h | 78 | 93 |
| Example 36 | 5 | Refined product | Commercial product | — | DCE(0.02M)/$H_2O$(50:1), 0° C., 18 h | 73 | 93 |
| Example 37 | 5 | Refined product | Commercial product | mCBA(1 eq) | DCE(0.02M)/$H_2O$(50:1), 0° C., 18 h | 69 | 92 |
| Example 38 | 5 | Refined product | Commercial product | mCBA(1 eq) + EtOH(6 eq) | DCE(0.02M)/$H_2O$(50:1), 0° C., 18 h | 81 | 95 |
| Example 39 | 5 | Refined product | Commercial product | — | DCE(0.02M), −20° C., 36 h | 83 | 93 |
| Example 40 | 5 | Refined product | Commercial product | EtOH(6 eq) | DCE(0.02M), −20° C., 36 h | 86 | 98 |

*1: m-CPBA (Aldrich) had a purity of 77% and included mCBA and water.
*2: A commercially available m—CPBA (Aldrich) was purified to have a purity of more than 99%.
*3: $CHCl_3$ (Nacalai) had a purity of 99% and included 1 percent by weight of EtOH serving as a stabilizer.
*4: A commercially available $CHCl_3$ (Nacalai) was distilled in such a way that EtOH was not included.
*5: A commercially available DCE (Wako Pure Chemical Industries, Ltd.) was used. A stabilizer was not included.

In Examples 23 to 27, various catalysts were examined. As a result, with respect to each of ethyl acetate, nitromethane, chloroform, and dichloroethane (DCE), a predetermined product was obtained at a high enantiomeric excess. In this regard, with respect to chloroform, in the case where the refined product was used, the yield decreased as compared with that of the commercially available product. The reason for this is considered that EtOH serving as a stabilizer contained in the commercially available product led to a good result.

In Examples 28 to 35, the solvent was fixed to be DCE, and various additives were examined. As a result, in the case where methanol, ethanol, isopropanol, isobutanol, or tert-butanol was added, the enantiomeric excess tended to increase, and the tendency was enhanced when the usage was 6 equivalents relative to 1-Naphthol compound S1. On the other hand, in the case where trifluoroacetic acid or acetic acid was used, such a tendency was not observed.

In Examples 36 to 38, influences of water and mCBA contained in the commercially available mCPBA were examined. As a result, adverse influences due to water and mCBA were not specifically observed. In this regard, in Example 38, the enantiomeric excess and the yield were improved because of addition of ethanol as compared with Example 37.

In Examples 39 and 40, the reaction temperature was examined. In Example 39, the reaction temperature in Example 27 was changed from 0° C. to −20° C., and in Example 40, the reaction temperature in Example 29 was changed from 0° C. to −20° C. The enantiomeric excess and the yield were at the same level.

[2-4] Examination of Reaction Substrate

Synthesis of optically active spirolactone compounds was performed by using various reaction substrates in conformity with the reaction example in Example 40 and, thereby, various products shown in Table 4 were obtained. In Examples 41 to 44, reaction substrates having a chloro group, a bromo group, or a phenyl group at position 4 of 1-naphthol were used. As a result, in every case, a product was obtained at very high enantiomeric excess and yield. In Examples 45 and 46, reaction substrates having a methoxy group at position 6 of 1-naphthol were used. In Example 47, a reaction substrate having a benzyloxymethyl group at position 3 of 1-naphthol was used. In Examples 48 and 49, reaction substrates having a 4-bromophenylcarbonyl group at position 4 of 1-naphthol were used. As a result, in every case, a product was obtained at a very high enantiomeric excess. In Example 50, a reaction substrate having a p-toluenesulfonylamino group (TsNH group) at position 5 of 1-naphthol was used. As a result, a product was obtained at a high enantiomeric excess.

TABLE 4

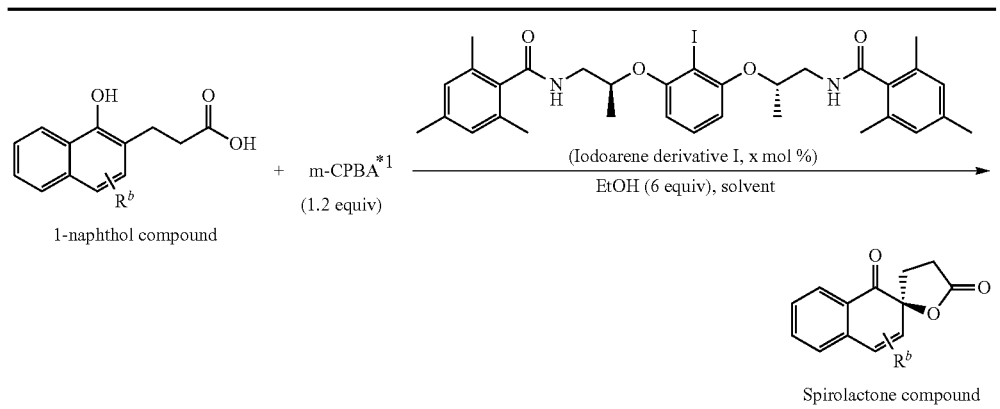

| | x | Reaction condition | Product | Yield (%) | ee(%) |
|---|---|---|---|---|---|
| Example 41 | 5 | DCE(0.02M), −20° C., 43 h | (4-Cl) | 67 | 98 |
| Example 42 | 10 | DCE(0.02M), −20° C., 23 h | | 93 | 98 |
| Example 43 | 5 | DCE(0.01M), −20° C., 24 h | (4-Br) | 99 | 95 |
| Example 44 | 5 | DCE(0.02M), −20° C., 43 h | (4-Ph) | 90 | 96 |
| Example 45 | 5 | DCE(0.02M), −20° C., 40 h | (6-MeO) | 50 | 98 |
| Example 46 | 10 | DCE(0.02M), −20° C., 23 h | | 73 | 98 |

TABLE 4-continued

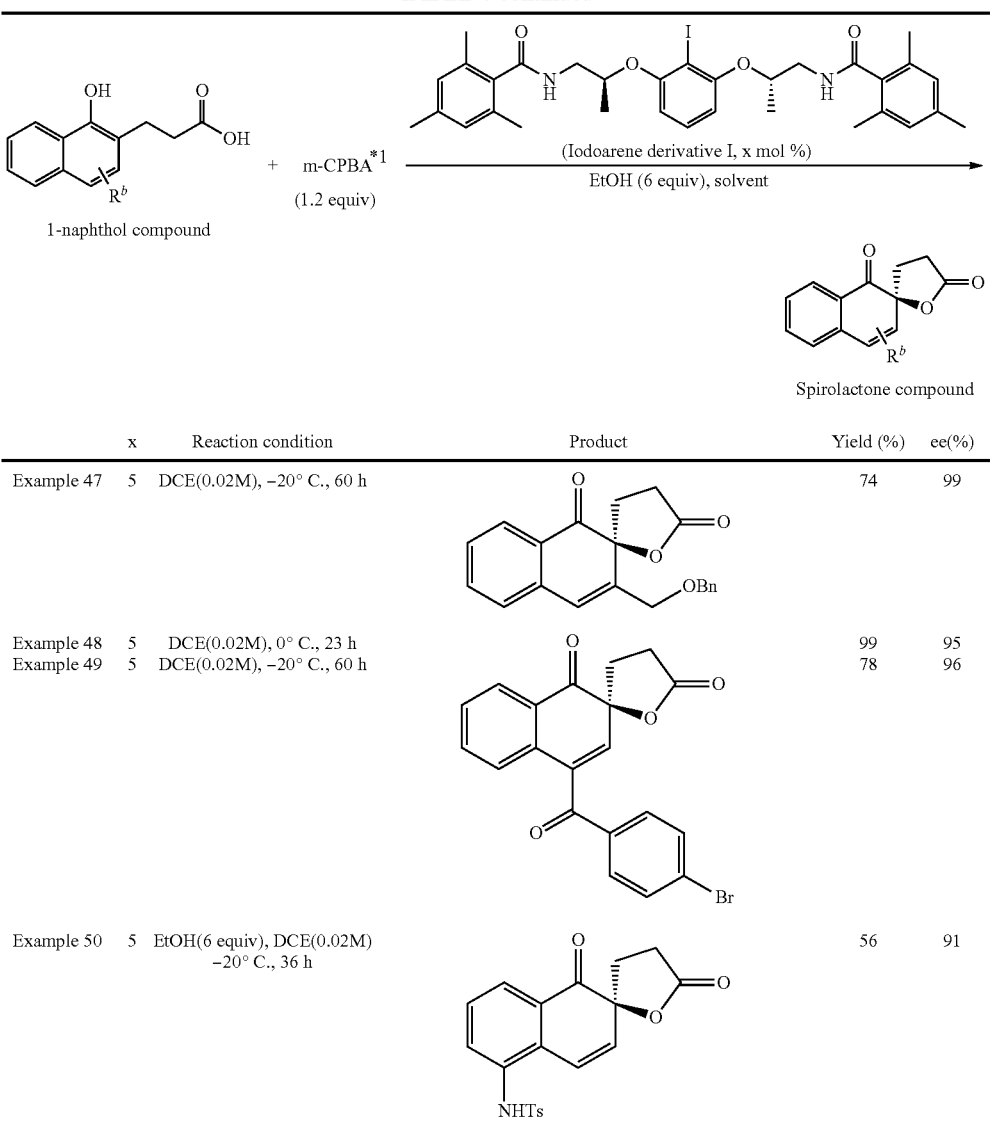

The spectrum data of the products obtained in Examples 41 to 50 are as described below.

Product in Examples 41 and 42: $^1$H NMR (CDCl$_3$, 400 MHz) δ 2.23 (ddd, J=9.6, 11.0, 13.4 Hz, 1H), 2.45 (ddd, J=2.3, 9.6, 13.4 Hz, 1H), 2.62 (ddd, J=2.3, 9.6, 17.9 Hz, 1H), 2.91 (ddd, J=9.6, 11.0, 17.9 Hz, 1H), 6.40 (s, 1H), 7.52 (dt, J=1.8, 7.4 Hz, 1H), 7.70-7.79 (m, 2H), 8.06 (d, J=7.4 Hz, 1H); $^{13}$C NMR (CDCl$_3$, 100 MHz) δ 26.5, 31.5, 83.4, 126.1, 127.3, 128.1, 129.1, 130.1, 131.8, 134.5, 135.8, 175.7, 194.7; HPLC (OD-H column), Hexane-EtOH=10:1 as eluent, 1.0 mL/min, $t_R$=23.4 min, $t_S$=25.7 min.

Product in Example 43: $^1$H NMR (CDCl$_3$, 400 MHz) δ 2.24 (ddd, J=9.6, 11.0, 13.5 Hz, 1H), 2.46 (ddd, J=2.3, 9.6, 13.5 Hz, 1H), 2.62 (ddd, J=2.3, 9.6, 17.9 Hz, 1H), 2.90 (ddd, J=9.6, 11.0, 17.9 Hz, 1H), 6.67 (s, 1H), 7.49-7.53 (m, 1H), 7.73-7.78 (m, 2H), 8.05 (d, J=7.2 Hz, 1H); $^{13}$C NMR (CDCl$_3$, 100 MHz) δ 26.8, 31.2, 84.2, 122.5, 127.0, 128.0, 128.8, 130.1, 133.4, 135.1, 135.9, 175.7, 194.7; HPLC (OD-H column), Hexane-EtOH=10:1 as eluent, 1.0 mL/min, $t_R$=24.7 min, $t_S$=28.4 min.

Product in Example 44: $^1$H NMR (CDCl$_3$, 400 MHz) δ 2.27 (ddd, J=9.6, 11.0, 13.3 Hz, 1H), 2.54 (ddd, J=2.3, 9.6, 13.3 Hz, 1H), 2.63 (ddd, J=2.3, 9.6, 17.6 Hz, 1H), 2.93 (ddd, J=9.6, 11.0, 17.6 Hz, 1H), 6.12 (s, 1H), 7.15 (d, J=7.3 Hz, 1H), 7.34-7.50 (m, 6H), 7.56 (dt, J=1.4, 7.3 Hz, 1H), 8.10 (dd, J=1.4, 7.3 Hz, 1H); $^{13}$C NMR (CDCl$_3$, 100 MHz) δ 26.7, 31.5, 83.7, 127.4, 127.6, 128.2, 128.4, 128.6 (2C), 128.7 (2C), 128.9, 130.6, 135.3, 137.4, 137.6, 139.8, 176.3, 196.4; HPLC (OD-H column), Hexane-EtOH=10:1 as eluent, 1.0 mL/min, $t_R$=21.7 min, $t_S$=27.1 min.

Product in Examples 45 and 46: $^1$H NMR (CDCl$_3$, 400 MHz) δ 2.17 (ddd, J=9.6, 11.0, 13.3 Hz, 1H), 2.40 (ddd, J=2.2, 9.6, 13.3 Hz, 1H), 2.61 (ddd, J=2.2, 9.6, 17.6 Hz, 1H), 2.95 (ddd, J=9.6, 11.0, 17.6 Hz, 1H), 3.94 (s, 3H), 6.21 (d, J=9.6 Hz, 1H), 6.60 (d, J=9.6 Hz, 1H), 6.72 (d, J=2.8 Hz, 1H), 6.91 (dd, J 2.8, 8.7 Hz, 1H), 8.01 (d, J=8.7 Hz, 1H); $^{13}$C NMR (CDCl$_3$, 100 MHz) δ 26.8, 31.6, 55.7, 82.8, 112.9, 114.2, 120.6, 127.9, 130.5, 133.3, 139.1, 165.6, 176.3, 194.8; HPLC (OD-H column), Hexane-i-PrOH=85:15 as eluent, 1.0 mL/min, $t_R$=30.7 min, $t_S$=35.6 min.

Product in Example 47: $^1$H NMR (CDCl$_3$, 400 MHz) δ 2.30-2.37 (m, 1H), 2.43-2.55 (m, 2H), 2.69-2.79 (m, 1H), 4.25 (d, J=12.8 Hz, 1H), 4.36 (d, J=12.8 Hz, 1H), 4.60 (s, 2H), 6.70 (s, 1H), 7.25 (d, J=7.8 Hz, 1H) 7.30-7.40 (m, 6H), 7.62 (t, J=7.8 Hz, 1H), 7.98 (d, J=7.8 Hz, 1H); $^{13}$C NMR (CDCl$_3$, 75 MHz) δ 26.1, 30.4, 68.9, 73.3, 85.8, 124.6, 126.7, 127.7, 127.8 (2C), 128.0 (2C), 128.5 (2C), 128.6 135.6, 136.8, 137.5, 140.0, 176.6, 196.9; HPLC (OD-H column), Hexane-i-PrOH=85:15 as eluent, 1.0 mL/min, $t_R$=20.8 min, $t_S$=38.3 min.

Product in Examples 48 and 49: $^1$H NMR (CDCl$_3$, 400 MHz) δ 2.27 (ddd, J=9.6, 11.0, 13.3 Hz, 1H), 2.52 (ddd, J=1.8, 9.6, 13.3 Hz, 1H), 2.63 (ddd, J=1.8, 9.6, 17.6 Hz, 1H), 2.92 (ddd, J=9.6, 11.0, 17.6 Hz, 1H), 6.38 (s, 1H), 7.37 (d, J=7.8 Hz, 1H), 7.50 (dt, J=0.9, 7.8 Hz, 1H), 7.60-7.66 (m, 3H), 7.83 (d, J=8.7 Hz, 1H), 8.12 (dd, J=1.4, 7.8 Hz, 1H); $^{13}$C NMR (CDCl$_3$, 100 MHz) δ 26.2, 31.2, 82.5, 126.8, 127.3, 128.6, 129.8, 129.9, 131.4 (2C), 132.3 (2C), 133.7, 134.2, 134.7, 135.8, 137.2, 175.7, 193.5, 195.0; HPLC (OD-H column), Hexane-i-PrOH=85:15 as eluent, 1.0 mL/min, $t_S$=44.3 min, $t_R$=49.7 min.

Product in Example 50: yellow solid; TLC, $R_f$=0.57 (hexane-EtOAc=1:2); IR (KBr) 3254, 1786, 1693, 1593, 1332, 1162 cm$^{-1}$; $^1$H NMR (CDCl$_3$, 400 MHz) δ 2.08-2.17 (m, 1H), 2.32-2.38 (m, 1H), 2.42 (s, 3H), 2.58 (ddd, J=1.8, 9.6. 17.8 Hz, 1H), 2.80-2.90 (m, 1H), 6.14 (d, J=10.6 Hz, 1H), 6.76 (d, J=10.6 Hz, 1H), 6.78 (s, 1H), 7.25-7.36 (m, 4H), 7.58 (d, J=8.3 Hz, 2H), 7.91 (d, J=6.9 Hz, 1H); $^{13}$C NMR (CDCl$_3$, 100 MHz) δ 21.6, 26.4, 31.2, 82.9, 122.1, 127.0, 127.3 (2C), 128.3, 129.2, 129.9 (2C), 132.3, 132.8, 133.3, 134.5, 135.6, 144.5, 176.3, 196.0; HPLC (IA-3 column), Hexane-EtOH=2:1 as eluent, 0.7 mL/min, $t_R$=47.0 min, $t_S$=75.1 min; HRMS (FAB) m/z calcd for C$_{20}$H$_{18}$NO$_5$S (M+H) 384.0906. found 384.0902; $[\alpha]^{27.9}{}_D$=−48.5 (c 0.80, CHCl$_3$) for 91% ee.

[3] Synthesis of Optically Active Spirolactone Compound by Oxidation of 2-Naphthol Compound

[3-1] Synthesis of 2-Naphthol Compound S2 (Refer to the Formula Described Below)

Acrylic acid (1.36 mL, 20.0 mmol) was added to a solution in which 2-naphthol (1.44 g, 10.0 mmol) and AMBERLIST (produced by Aldrich, strong acid, 1.0 g) serving as an ion-exchange resin were dissolved into toluene (30 mL), while the solution was agitated. The resulting mixed solution was refluxed for a day. The resulting suspension was filtrated through celite, and the solvent was removed by distillation in a vacuum. The residue was refined by silica gel flash chromatography (dissolution medium hexane-EtOAc=20:1 (v/v)) to obtain a pyran derivative (1.78 g, 9.0 mmol, yield 90%). A solution in which the resulting pyran derivative (1.78 g, 9.0 mmol) was dissolved into THF (40 mL) was blended with 1-N LiOH (30 mL) and the resulting reaction mixed solution was agitated at room temperature for 6 hours. The resulting reaction mixed solution was poured into 1-N HCl (100 mL), extraction with EtOAc was performed two times, and washing was performed with a saline solution. Organic layers were mixed and dried with anhydrous Na$_2$SO$_4$. The solvent was removed by distillation in a vacuum. The residue was refined by silica gel flash chromatography (dissolution medium hexane-EtOAc=4:1 to 1:1 (v/v)) to obtain 2-Naphthol compound S2, that is, 3-(2-hydroxynaphthalen-1-yl)propanoic acid (4.05 g, 18.7 mmol) at a yield of 62%. The spectrum data thereof are as described below. In this regard, various 2-naphthol compounds used as starting materials in examples described later were synthesized by this method.

2-Naphthol compound S2: $^1$H NMR (CDCl$_3$, 400 MHz) δ 2.95 (t, J=6.4 Hz, 2H), 3.33 (t, J=6.4 Hz, 2H), 7.15 (d, J=8.4 Hz, 1H), 7.35 (t, J=8.4 Hz, 1H), 7.50 (t, J=8.4 Hz, 1H), 7.67 (d, J=8.4 Hz, 1H), 7.78 (d, J=8.4 Hz, 2H); $^{13}$C NMR (CDCl$_3$, 100 MHz) δ 19.4, 33.5, 117.9, 119.4, 122.0, 123.2, 126.7, 128.7, 128.9, 129.5, 132.7, 151.6, 180.4.

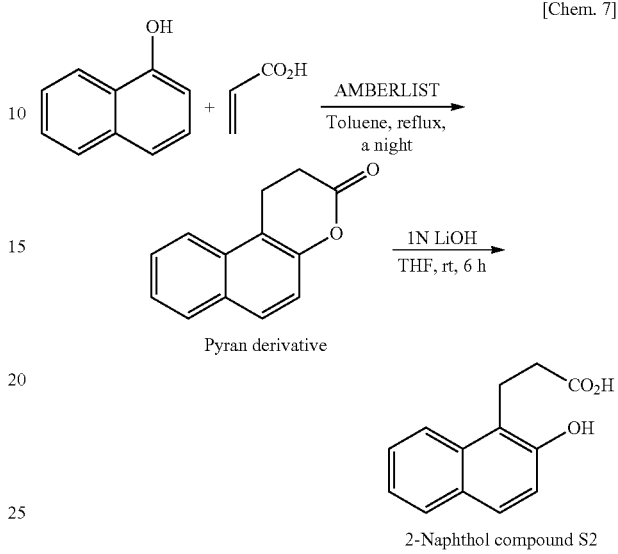

[Chem. 7]

Pyran derivative

2-Naphthol compound S2

[3-2] Synthesis Examples by Using Various Catalyst Precursors and Various Reaction Substrates Synthesis of optically active spirolactone compounds was performed by using various 2-naphthol compounds as reaction substrates in conformity with the reaction example in Example 40 and, thereby, various products shown in Table 5 were obtained. Here, Catalyst precursors I and M were used. In this regard, in the case where the 2-naphthol compound was used as the reaction substrate, an effect of adding an alcohol was not observed, so that alcohol was not added. In Examples 51 and 52, 2-Naphthol compound S2 was used as the reaction substrate, and products were obtained at high enantiomeric excesses and good yields. In particular, in Example 52, a mixed solvent of DCE and HFIP was used as the reaction solvent and, thereby, both the yield and the enantiomeric excess were improved as compared with those in Example 51 in which a DCE single solvent was used. In Examples 53 to 57, reaction substrates having a bromo group at position 3, position 6, or position 7 of the 2-naphthol compound were used, and in every case, a product was obtained at a high enantiomeric excess. In this regard, in the case where the reaction substrate having a bromo group at position 7 was used, the yield decreased. However, in the case where the reaction substrates having a bromo group at position 3 or position 6 were used, the yields were also good. In Examples 58 and 59, reaction substrates having a methoxy group at position 7 or position 4 of the 2-naphthol compound were used, and in every case, a product was obtained at a high enantiomeric excess. In this regard, in the case where the reaction substrate having a methoxy group at position 4 was used, the yield decreased. However, in the case where the reaction substrate having a methoxy group at position 7 was used, the yield was also good. In Examples 60 to 63, 2-naphthol compounds having a fluoro group at position 8, a methyl group at position 4, a benzyloxy group at position 7, and a methoxymethoxy group at position 7, respectively, are used as the reaction substrates. As a result, in every case, a product was obtained at a high yield and a high enantiomeric excess.

TABLE 5

Iodoarene derivative I: Ar = 2,4,6-trimethylphenyl (mesityl)

M: Ar = anthracen-9-yl 2-naphthol compound + m-CPBA (1.2 equiv) → Spirolactone compound

DCE (0.02M), -20° C.

| | Reaction condition | Product | Yield (%) | ee(%) |
|---|---|---|---|---|
| Example 51 | Iodoarene M(10 mol %), 18 h | | 72 | 89 |
| Example 52 | Iodoarene I(10 mol %), 13 h *2 | | 93 | 94 |
| Example 53 | Iodoarene M(10 mol %), 24 h | | 90 | 78 |
| Example 54 | Iodoarene I(10 mol %), 24 h | (Br-substituted) | 90 | 91 |
| Example 55 | Iodoarene M(10 mol %), 24 h | (Br-substituted) | 64 | 86 |
| Example 56 | Iodoarene M(10 mol %), 24 h | | 36 | 71 |
| Example 57 | Iodoarene I(10 mol %), 24 h | (Br-substituted) | 10 | 78 |
| Example 58 | Iodoarene M(10 mol %), 24 h | (MeO-substituted) | 80 | 89 |

TABLE 5-continued
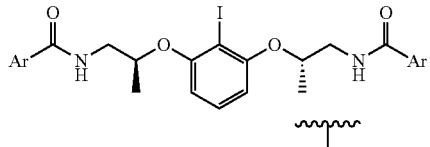
| | Reaction condition | Product | Yield (%) | ee(%) |
|---|---|---|---|---|
| Example 59 | Iodoarene M(10 mol %), 13 h | 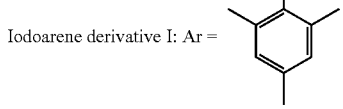 | 23 | 92 |
| Example 60 | Iodoarene M(10 mol %), 22 h | 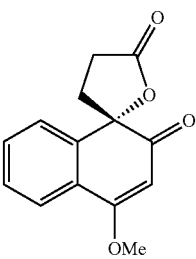 [SMILES: COC1=CC(=O)[C@]2(CCC(=O)O2)c2ccccc21] | 68 | 83 |
| Example 61 | Iodoarene M(10 mol %), 19 h | 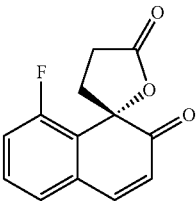 [SMILES: O=C1CC[C@@]2(O1)C(=O)C=Cc1cccc(F)c12] | 80 | 95 |
| Example 62 | Iodoarene M(10 mol %), 16 h | 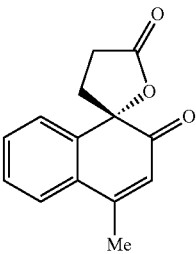 [SMILES: CC1=CC(=O)[C@]2(CCC(=O)O2)c2ccccc21] | 66 | 87 |

TABLE 5-continued

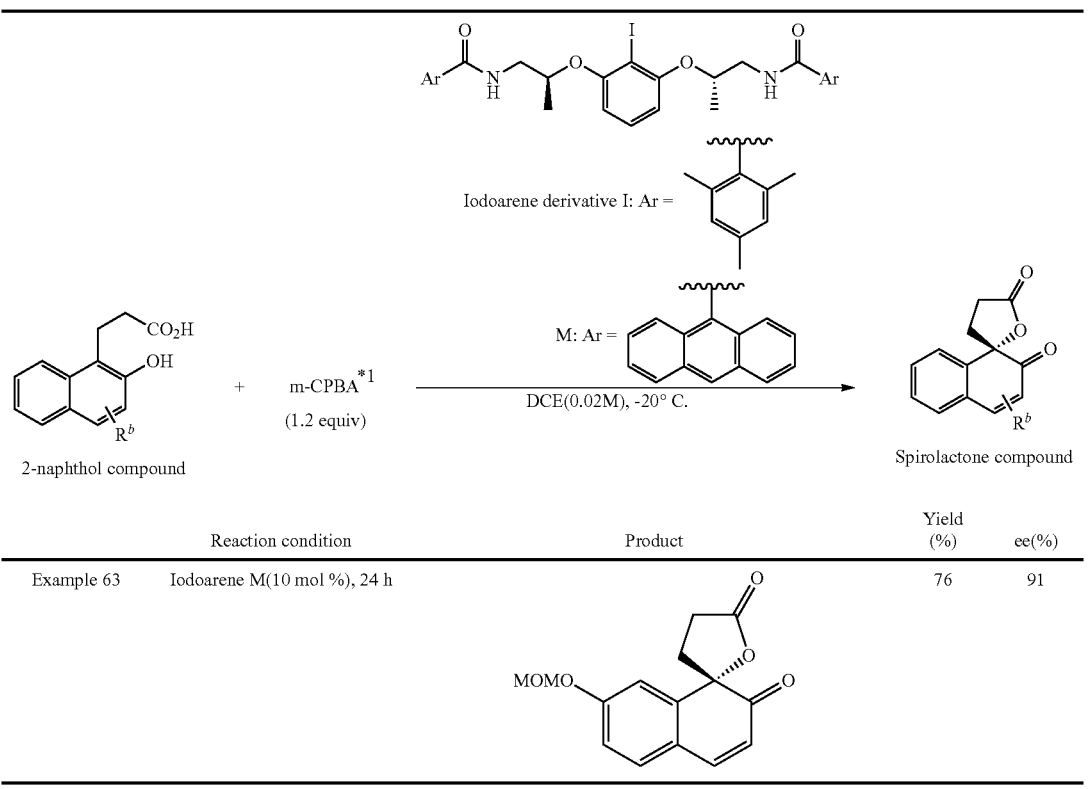

*1: A commercially available m-CPBA (Aldrich) was purified to have a purity of more than 99%.
*2: DCE/HFIP (9:1 v/v, 0.02M) was used as a reaction solvent.

The spectrum data of the products obtained in Examples 51 to 63 are as described below.

Product in Examples 51 and 52: $^1$H NMR (CDCl$_3$, 400 MHz) δ 2.11-2.20 (m, 1H), 2.62-2.70 (m, 2H), 2.81-2.91 (m, 1H), 6.18 (d, J=9.6 Hz, 1H), 7.36 (dd, J=1.6, 7.6 Hz, 1H), 7.41 (dt, J=1.6, 7.6 Hz, 1H), 7.46-7.50 (m, 2H), 7.56 (d, J=7.6 Hz, 1H); $^{13}$C NMR (CDCl$_3$, 100 MHz) δ 26.5, 35.7, 85.8, 122.4, 125.6, 129.0, 129.1, 129.7, 131.0, 140.4, 146.0, 176.4, 197.5; HPLC (OD-H column), Hexane-EtOH=10:1 as eluent, 1.0 mL/min, $t_S$=28.6 min, $t_R$=41.6 min.

Product in Examples 53 and 54: $^1$H NMR (CDCl$_3$, 400 MHz) δ 2.15-2.23 (m, 1H), 2.64-2.72 (m, 2H), 2.82-2.92 (m, 1H), 7.33 (d, J=7.2 Hz, 1H), 7.42 (dt, J=1.6, 7.2 Hz, 1H), 7.51 (dt, J=1.6, 7.2 Hz, 1H), 7.55 (dd, J=1.6, 7.2 Hz, 1H), 7.92 (s, 1H); $^{13}$C NMR (CDCl$_3$, 100 MHz) δ 26.4, 36.1, 86.4, 118.2, 126.0, 128.8, 129.4, 129.6, 131.4, 139.9, 147.3, 175.9, 191.2; HPLC (OD-H column), Hexane-EtOH=10:1 as eluent, 1.0 mL/min, $t_S$=32.1 min, $t_R$=46.7 min.

Product in Example 55: $^1$H NMR (CDCl$_3$, 400 MHz) δ 2.08-2.17 (m, 1H), 2.62-2.69 (m, 2H), 2.79-2.89 (m, 1H), 6.22 (d, J=9.6 Hz, 1H), 7.41 (d, J=9.6 Hz, 1H), 7.44 (d, J=8.4 Hz, 1H), 7.51 (d, J=1.8 Hz, 1H), 7.60 (dd, J=1.8, 8.4 Hz, 1H); $^{13}$C NMR (CDCl$_3$, 100 MHz) δ 26.4, 35.6, 85.4, 123.1, 123.8, 127.4, 130.9, 132.3, 133.7, 139.2, 144.4, 176.0, 196.7; HPLC (OD-H column), Hexane-EtOH=10:1 as eluent, 1.0 mL/min, $t_S$=34.0 min, $t_R$=42.2 min.

Product in Examples 56 and 57: $^1$H NMR (CDCl$_3$, 400 MHz) δ 2.11-2.20 (m, 1H), 2.63-2.70 (m, 2H), 2.80-2.90 (m, 1H), 6.21 (d, J=10.1 Hz, 1H), 7.22 (d, J=7.8 Hz, 1H), 7.44 (d, J=10.1 Hz, 1H), 7.54 (dd, J=1.8, 7.8 Hz, 1H), 7.72 (d, J=1.8 Hz, 1H); $^{13}$C NMR (CDCl$_3$, 100 MHz) δ 26.4, 35.7, 85.1, 122.8, 125.8, 128.0, 129.1, 130.9, 132.4, 142.3, 144.9, 175.9, 196.5; HPLC (AS-H column), Hexane-EtOH=10:1 as eluent, 0.7 mL/min, $t_R$=38.9 min, $t_S$=50.6 min.

Product in Example 58: $^1$H NMR (CDCl$_3$, 400 MHz) δ 2.09-2.18 (m, 1H), 2.61-2.70 (m, 2H), 2.79-2.89 (m, 1H), 3.87 (s, 3H), 6.04 (d, J=9.6 Hz, 1H), 6.88 (dd, J=1.8, 8.7 Hz, 1H), 7.08 (d, J=1.8 Hz, 1H), 7.28 (d, J=8.7 Hz, 1H), 7.43 (d, J=9.6 Hz, 1H); $^{13}$C NMR (CDCl$_3$, 100 MHz) δ 26.5, 36.1, 55.7, 86.0, 111.5, 114.4, 119.7, 122.1, 131.5, 143.0, 146.0, 162.1, 176.5, 197.5; HPLC (OD-H column), Hexane-EtOH=10:1 as eluent, 1.0 mL/min, $t_S$=32.5 min, $t_R$=41.0 min.

Product in Example 59: $^1$H NMR (CDCl$_3$, 400 MHz) δ 2.14-2.23 (m, 1H), 2.61-2.70 (m, 2H), 2.91-3.01 (m, 1H), 3.99 (s, 3H), 5.60 (s, 1H), 7.42-7.48 (m, 1H), 7.52-7.57 (m, 2H), 7.86 (d, J=7.8 Hz, 1H); $^{13}$C NMR (CDCl$_3$, 100 MHz) δ 27.2, 36.8, 56.6, 84.6, 96.9, 124.3, 125.5, 126.7, 128.7, 131.7, 140.0, 168.7, 176.8, 196.0; HPLC (OD-H column), Hexane-EtOH=10:1 as eluent, 1.0 mL/min, $t_R$=36.2 min, $t_S$=58.9 min.

Product in Example 60: white solid; TLC, $R_f$=0.57 (hexane-EtOAc=1:2); IR (KBr) 1787, 1674, 1573, 1463, 1399, 1247, 1179 cm$^{-1}$; $^1$H NMR (CDCl$_3$, 400 MHz) δ 2.41-2.56 (m, 2H), 2.78 (ddd, J=3.2, 10.1, 17.4 Hz, 1H), 2.99 (dt, J=10.6, 17.4 Hz, 1H), 6.23 (d, J=10.1 Hz, 1H), 7.16-7.21 (m, 2H), 7.41-7.46 (m, 1H), 7.48 (dd, J=1.8, 10.1 Hz, 1H); $^{13}$C NMR (CDCl$_3$, 100 MHz) δ 27.1, 32.6, 81.0, 118.8 (d, $J_{C-F}$=22 Hz), 123.8, 125.8 (d, $J_{C-F}$=3 Hz), 126.2 (d, $J_{C-F}$=10 Hz), 131.3, 131.4, 145.5 (d, $J_{C-F}$=4 Hz), 161.5, (d, $J_{C-F}$=251 Hz), 176.4, 196.3; $^{19}$F NMR (CDCl$_3$, 376 MHz) d=111.5; HRMS (FAB) m/z calcd for C$_{13}$H$_{10}$FO$_3$ (M+H) 233.0614. found 233.0620; HPLC (IA-3 column), Hexane-EtOH=4:1 as eluent, 1.0 mL/min, $t_R$=18.9 min, $t_S$=21.3 min; $[α]^{28.8}_D$=103.8 (c 1.5, CHCl$_3$) for 83% ee.

Product in Example 61: white solid; TLC, $R_f$=0.57 (hexane-EtOAc=1:2); IR (KBr) 1786, 1673, 1617, 1246, 1171, 1037 cm$^{-1}$; $^1$H NMR (CDCl$_3$, 400 MHz) δ 2.10-2.19 (m, 1H), 2.40 (s, 3H), 2.56-2.68 (m, 2H), 2.81-2.91 (m, 1H), 6.11 (s, 1H), 7.43 (dt, J=1.4, 7.3 Hz, 1H), 7.49 (dt, J=1.4, 7.3 Hz, 1H), 7.56-7.58 (m, 2H); $^{13}$C NMR (CDCl$_3$, 100 MHz) δ 20.5, 26.8, 36.1, 85.7, 122.0, 125.6, 126.0, 128.9, 130.4, 130.8, 140.3, 154.0, 176.5, 196.7; HRMS (FAB) m/z calcd for C$_{14}$H$_{13}$O$_3$ (M+H) 229.0865. found 229.0871; HPLC (IA-3 column), Hexane-EtOH=4:1 as eluent, 1.0 mL/min, t$_R$=17.4 min, t$_S$=18.8 min; [α]$^{28.7}_D$=−333.3 (c 1.6, CHCl$_3$) for 95% ee.

Product in Example 62: yellow solid; TLC, R$_f$=0.63 (hexane-EtOAc=1:2); IR (KBr) 1786, 1673, 1602, 1292, 1169, 1037 cm$^{-1}$; $^1$H NMR (CDCl$_3$, 400 MHz) δ 2.06-2.15 (m, 1H), 2.58-2.68 (m, 2H), 2.78-2.88 (m, 1H), 5.12 (s, 2H), 6.04 (d, J=10.1 Hz, 1H), 6.95 (dd, J=2.3, 8.2 Hz, 1H), 7.17 (d, J=2.3 Hz, 1H), 7.27 (d, J=8.2 Hz, 1H), 7.32-7.44 (m, 6H); $^{13}$C NMR (CDCl$_3$, 100 MHz) δ 26.5, 36.1, 70.4, 85.9, 112.6, 115.1, 119.9, 122.4, 127.5 (2C), 128.3, 128.7 (2C), 131.5, 135.9, 143.0, 145.9, 161.2, 176.4, 197.4; HRMS (FAB) m/z calcd for C$_{20}$H$_{17}$O$_4$ (M+14) 321.1127. found 321.1124; HPLC (OD-H column), Hexane-EtOH=4:1 as eluent, 1.0 mL/min, t$_S$=16.3 min, t$_R$=20.0 min; [α]$^{25.2}_D$=−133.5 (c 1.8, CHCl$_3$) for 87% ee.

Product in Example 63: yellow solid; TLC, R$_f$=0.50 (hexane-EtOAc=1:2); IR (KBr) 1786, 1675, 1603, 1559, 1169 cm$^{-1}$; $^1$H NMR (CDCl$_3$, 400 MHz) δ 2.05-2.19 (m, 1H), 2.61-2.69 (m, 2H), 2.79-2.89 (m, 1H), 3.48 (s, 3H), 5.19 (d, J=6.9 Hz, 1H), 5.25 (d, J=6.9 Hz, 1H), 6.06 (d, J=9.6 Hz, 1H), 7.04 (dd, J=2.8, 8.7 Hz, 1H), 7.20 (d, J=2.8 Hz, 1H), 7.26 (d, J=8.7 Hz, 1H), 7.43 (d, J=9.6 Hz, 1H); $^{13}$C NMR (CDCl$_3$, 100 MHz) δ 26.5, 36.0, 56.3, 85.8, 94.1, 114.0, 116.0, 120.2, 123.1, 131.4, 142.8, 145.8, 159.6, 176.4, 197.4; HRMS (FAB) m/z calcd for C$_{15}$H$_{15}$O$_5$ (M+H) 275.0919. found 275.0921; HPLC (IA-3 column), Hexane-EtOH=4:1 as eluent, 1.0 mL/min, t$_S$=33.1 min, t$_R$=45.1 min; [α]$^{23.7}_D$=−239.8 (c 1.7, CHCl$_3$) for 91% ee.

[4] Synthesis and Reaction of Hypervalent Iodine Compound

Trivalent hypervalent iodine compounds (Iodoarene derivatives I' and M') were synthesized from Catalyst precursors I and M.

Iodoarene Derivative I'

Synthesis from Iodoarene derivative I was performed following the reaction formula described below. That is, a solution in which Iodoarene derivative I (0.64 g, 1.0 mmol) was dissolved into peracetic acid (solution having a concentration of 9% in acetic acid, 8 mL, ca. 10 mmol) was agitated at room temperature for a night. The resulting mixed solution was diluted with CH$_2$Cl$_2$ and was washed two times with distilled water. An organic layer was dried with anhydrous Na$_2$SO$_4$, and the solvent was removed by distillation in a vacuum, so as to obtain Iodoarene derivative I' (0.72 g, 0.94 mmol) at a yield of 94% and the purity of more than 99% (on the basis of $^1$H NMR analysis). The spectrum data of Iodoarene derivative I' are as described below.

$^1$H NMR (CDCl$_3$, 400 MHz) δ 1.30 (s, 6H), 1.46 (d, J=6.4 Hz, 6H), 2.11 (s, 12H), 2.20 (s, 6H), 3.42-3.49 (m, 2H), 4.07 (ddd, J=2.8, 7.6, 14.2 Hz, 2H), 4.81-4.83 (m, 2H), 6.70 (d, J=8.4 Hz, 2H), 6.71-6.74 (m, 2H), 6.74 (s, 4H), 7.48 (t, J=8.4 Hz, 1H).

Synthesis of Iodoarene Derivative M'

Iodoarene derivative M' was synthesized from Iodoarene derivative M, following the reaction formula described below, in conformity with the synthesis of Iodoarene derivative I'. The yield was 90%. The spectrum data of Iodoarene derivative M' are as described below.

$^1$H NMR (CDCl$_3$, 400 MHz) δ 0.55 (s, 6H), 1.46 (d, J=6.4 Hz, 6H), 3.61 (ddd, J=4.4, 8.4, 14.0 Hz, 2H), 4.33 (ddd, J=2.4, 7.6, 14.0 Hz, 2H), 5.04-5.07 (m, 2H), 6.86 (d, J=8.4 Hz, 2H), 7.00-8.10 (m, 18H), 7.63 (t, J=8.4 Hz, 1H), 8.39 (s, 2H).

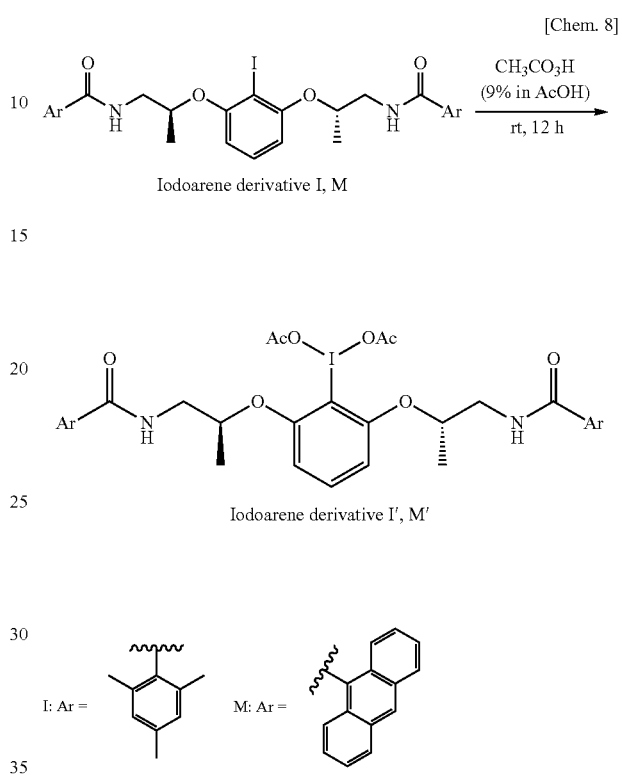

[Chem. 8]

Synthesis of optically active spirolactone compounds was performed by using Iodoarene derivatives I' and M' described above, while the 1-naphthol compound or the 2-naphthol compound served as the reaction substrate, and thereby, various products of Examples 64 to 70 shown in Table 6 were obtained. In Examples 64 to 70, the reaction conditions shown in Table 6 were adopted in conformity with the reaction example in Example 40. Here, Iodoarene derivatives I' and M' were specified to be stoichiometric quantities (1 equivalent) relative to the reaction substrate. In every Example, a predetermined product was obtained at good enantiomeric excess and yield. Consequently, it was found that Iodoarene derivatives I' and M' were able to be utilized for the spirolactonization reaction. In particular, in Examples 65, 66, 67, and 70, when Iodoarene derivatives I and M having a monovalent iodine atom and m-CPBA were used, the reaction did not proceed smoothly because the reaction substrate reacted with m-CPBA or the spirolactone compound reacted with m-CPBA. However, when Iodoarene derivatives I' and M' having a trivalent iodine atom were used, the reaction proceeded smoothly.

TABLE 6

Iodoarene derivative I' : Ar = (mesityl) (1 equiv)

M' : Ar = (anthracen-9-yl)

| | Reaction condition | Product | Yield (%) | ee (%) |
|---|---|---|---|---|
| Example 64 | Iodoarene I' (1 equiv), EtOH (6 equiv), DCE (0.02M), −20° C., 4 h | (structure) | 90 | 98 |
| Example 65 | Iodoarene I' (1 equiv), EtOH (6 equiv), DCE (0.01M), 0° C., 21 h | (structure) | 71 | 97 |
| Example 66 | Iodoarene I' (1 equiv), EtOH (6 equiv), DCE (0.01M), 0° C., 21 h | (structure) | 72 | 54 |
| Example 67 | Iodoarene I' (1 equiv), EtOH (6 equiv), DCE (0.02M), −20° C., 16 h | (structure, OMe) | 90 | 99 |
| Example 68 | Iodoarene I' (1 equiv), DCE (0.02M), 20° C., 18 h | (structure) | 71 | 75 |
| Example 69 | Iodoarene M' (1 equiv), DCE (0.02M), −20° C., 18 h | (structure) | 72 | 80 |
| Example 70 | Iodoarene I' (1 equiv), DCE (0.01M), rt, 24 h | (structure) | 84 | 51 |

The spectrum data of the products obtained in Examples 65, 66, 67, and 70 are as described below.

Product in Example 65: $^1$H NMR (CDCl$_3$, 400 MHz) δ 2.25 (ddd, J=9.6, 11.6, 13.6 Hz, 1H), 2.44 (ddd, J=2.4, 9.6, 13.6 Hz, 1H), 2.64 (ddd, J=2.4, 9.6, 17.2 Hz, 1H), 2.91 (ddd, J=9.6, 11.6, 17.2 Hz, 1H), 6.51 (d, J=10.0 Hz, 1H), 6.90 (d, J=10.0 Hz, 1H), 7.36 (dd, J=4.6, 8.0 Hz, 1H), 8.27 (dd, J=1.8, 8.0 Hz, 1H), 8.82 (dd, J=1.8, 4.6 Hz, 1H); $^{13}$C NMR (CDCl$_3$, 100 MHz) δ 26.2, 31.1, 82.9, 123.5, 123.6, 129.7, 135.2, 136.3, 155.5 (2C), 176.0, 196.1; HPLC (OD-H column), Hexane-EtOH=2:1 as eluent, 0.7 mL/min, $t_R$=16.5 min, $t_S$=24.8 min.

Product in Example 66: $^1$H NMR (CDCl$_3$, 400 MHz) 2.22 (ddd, J=9.6, 11.6, 13.4 Hz, 1H), 2.51 (ddd, J=1.8, 9.6, 13.4 Hz, 1H), 2.61 (ddd, J=1.8, 9.6, 17.8 Hz, 1H), 2.92 (ddd, J=9.6, 11.6, 17.8 Hz, 1H), 6.34 (d, J=10.1 Hz, 1H), 6.63 (d, J=10.1 Hz, 1H), 7.54 (dd, J=4.6, 7.8 Hz, 1H), 7.66 (dd, J=1.4, 7.8 Hz, 1H), 8.75 (dd, J=1.4, 4.6 Hz, 1H); $^{13}$C NMR (CDCl$_3$, 100 MHz) δ 26.0, 30.9, 84.7, 125.7, 128.6, 134.1 (2C), 135.6, 136.3, 150.5, 176.0, 195.0; HPLC (AD-H column), Hexane-EtOH=2:1 as eluent, 0.7 mL/min, $t_S$=35.6 min, $t_R$=42.9 min.

Product in Example 67: $^1$H NMR (CDCl$_3$, 400 MHz) δ 2.34-2.48 (m, 2H), 2.70 (ddd, J=5.0, 9.6, 17.6 Hz, 1H), 2.87 (ddd, J=8.2, 10.6, 17.6 Hz, 1H), 3.82 (s, 3H), 5.73 (s, 1H), 7.15 (d, J=7.3 Hz, 1H), 7.23 (dt, J=0.9, 7.3 Hz, 1H), 7.54 (dt, J=1.4, 7.3 Hz, 1H), 7.95 (d, J=7.3 Hz, 1H; $^{13}$C NMR (CDCl$_3$, 100 MHz) δ 27.4, 30.5, 55.8, 82.8, 98.3, 124.7, 126.4, 126.8, 128.1, 136.0, 138.2, 157.6, 176.6, 195.2; HPLC (AB-3 column), Hexane-i-PrOH=85:15 as eluent, 0.7 mL/min, $t_S$=40.0 min, $t_R$=42.2 min.

Product in Example 70: $^1$H NMR (CDCl$_3$, 400 MHz) δ 2.12-2.23 (m, 1H), 2.63-2.75 (m, 2H), 2.83-2.93 (m, 1H), 6.42 (d, J=10.1 Hz, 1H), 7.39 (dd, J=5.0, 7.8 Hz, 1H), 7.69 (d, J=10.1 Hz, 1H), 7.88 (dd, J=0.9, 7.8 Hz, 1H), 8.66 (d, J=0.9, 5.0 Hz, 1H); $^{13}$C NMR (CDCl$_3$, 100 MHz) δ 26.3, 35.1, 84.7, 124.6, 126.1, 133.1, 136.7, 147.3, 148.1, 150.4, 175.8, 196.4; HPLC (OD-H column), Hexane-EtOH=2:1 as eluent, 0.7 mL/min, $t_S$=16.5 min, $t_R$=40.7 min.

The results shown in Table 6 indicate that in the spirolactonization reaction (catalytic enantioselective dearomatization type oxidation reaction) by using various Iodoarene derivatives A to V, catalysts (for example, Iodoarene derivatives I' and M'), which are trivalent hypervalent iodine compounds, are generated by oxidation of Iodoarene derivatives A to V serving as catalyst precursors by m-CPBA in the system, the resulting catalysts oxidize and, at the same time, aromatize the naphthol compounds to convert to corresponding spirolactone compounds, while the catalysts in themselves are reduced to return to the catalyst precursors, i.e. Iodoarene derivatives, again (refer to the following formula). In this regard, both $L^1$ and $L^2$ may be an acyloxy group (acyloxy group derived from a carboxylic acid of mCBA or the reaction substrate), one of them may be OH and the other may be an acyloxy group, or both of them may be OH.

Reaction mechanism

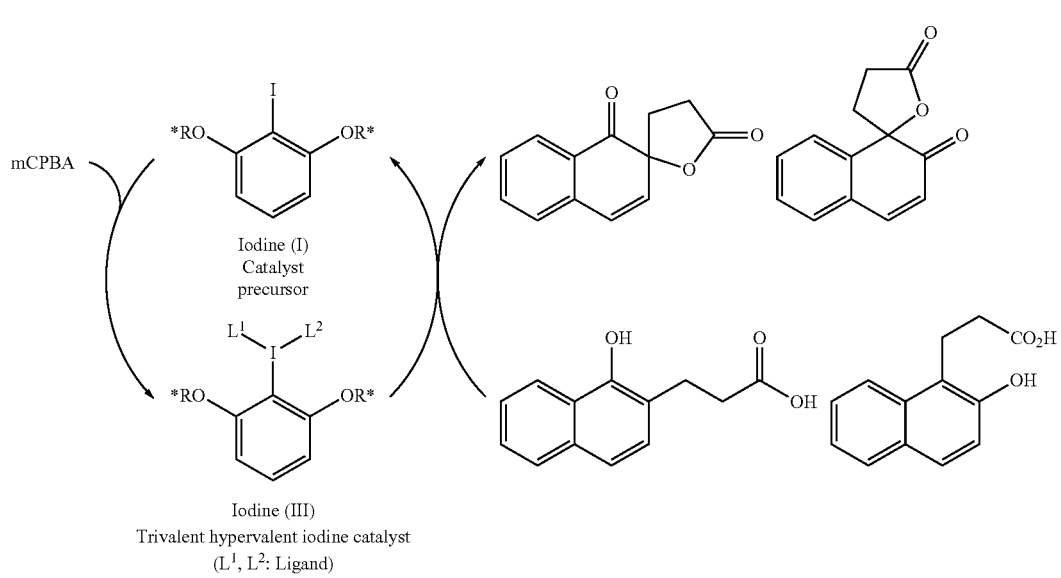

[Chem. 9]

[5] Synthesis of Optically Active Spirolactone Compound by Oxidation of Phenol Compound

[5-1] Oxidation of Phenol Compound in which OH Group is Bonded to Position 1 and (CH$_2$)$_2$COOH is Bonded to Position 2

Synthesis of optically active spirolactone compounds was performed by using various phenol compounds, in which a OH group was bonded to position 1 and (CH$_2$)$_2$COOH was bonded to position 2, as reaction substrates in conformity with the reaction example in Example 40 and, thereby, various products shown in Table 7 were obtained. In Examples 71, 73, 75, 77, and 78, Iodoarene derivative I was used. In Examples 72, 74, and 76, Iodoarene derivative I' was used. In Examples 71, 72, 76, and 77, alcohol was added. Meanwhile, a mixed solvent of DCE and nitromethane was used in Examples 74 and 75, a DCE single solvent was used in Examples 71 to 73 and 76, a dichloromethane (DCM) single solvent was used in Example 77, and a mixed solvent of DCM and HFIP was used in Example 78. According to the results shown in Table 7, in every case, an optically active spirolactone compound was obtained at a high enantiomeric excess. In this regard, the yield in the case where Iodoarene derivative I' was used was higher than the yield in the case where Iodoarene derivative I was used, although depending on the reaction substrate (Examples 71 and 72 and Examples 73 and 74).

TABLE 7

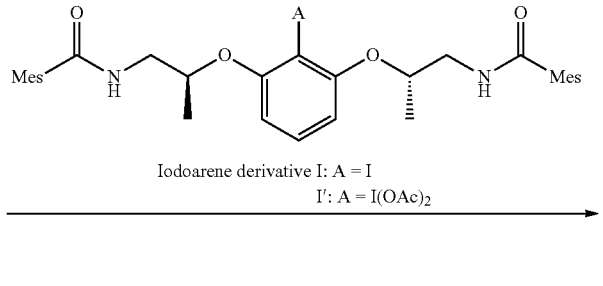

| | Reaction condition | Spirolactone compound | Yield (%) | ee(%) |
|---|---|---|---|---|
| Example 71 | mCPBA(1.2 equiv) *1<br>Iodoarene I(5 mol %)<br>EtOH(6 equiv), DCE(0.02M), −20° C., 36 h | 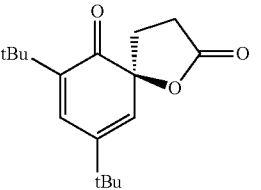 [SMILES: CC(C)(C)C1=C[C@@]2(CCC(=O)O2)C(=O)C(C(C)(C)C)=C1] | 46 | 89 |
| Example 72 | Iodoarene I' (1 equiv)<br>EtOH(6 equiv), DCE(0.02M), −20° C., 15 h | | 90 | 86 |
| Example 73 | mCPBA(1.2 equiv) *1<br>Iodoarene I(10 mol %)<br>DCE(0.02M), −20° C., 25 h | 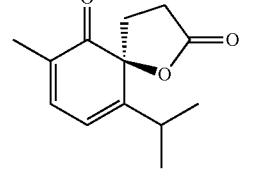 | 36 | 89 |
| Example 74 | Iodoarene I' (1 equiv)<br>DCE/CH$_3$NO$_2$(2:1 v/v, 0.01M), −20° C., 2 h | | 65 | 81 |
| Example 75 | mCPBA(1.2 equiv) *1<br>Iodoarene I(10 mol %)<br>DCE/CH$_3$NO$_2$(2:1 v/v, 0.01M), −20° C., 23 h | 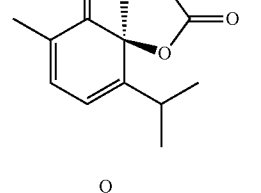 | 86 | 97 |
| Example 76 | Iodoarene I' (1 equiv)<br>EtOH(6 equiv), DCE(0.02M), −20° C., 1 h | 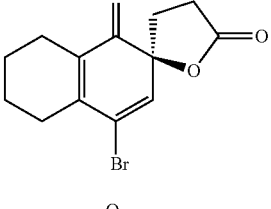 | 23 | 73 |
| Example 77 | mCPBA(1.2 equiv) *1<br>Iodoarene I(10 mol %)<br>EtOH(6 equiv), DCM(0.02M), −20° C., 30 h | 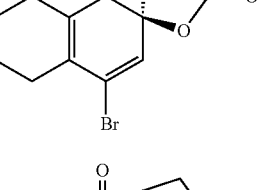 | 56 | 91 |
| Example 78 | mCPBA(1.2 equiv) *1<br>Iodoarene I(5 mol %)<br>DCM/HFIP(9:1 v/v, 0.02M), −20° C., 23 h | 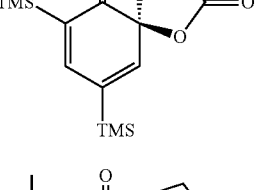 | 58 | 70 |

*1: A commercially available m-CPBA (Aldrich) was purified to have a purity of more than 99%.

The spectrum data of the products obtained in Examples 71 to 78 are as described below.

Product in Examples 71 and 72: yellow solid; TLC, $R_f$=0.57 (hexane-EtOAc=1:2); IR (KBr) 2959, 1791, 1673, 1366, 1160 cm$^{-1}$; $^1$H NMR (CDCl$_3$, 400 MHz) δ 1.15 (s, 9H), 1.23 (s, 9H), 1.98-2.03 (m, 1H), 2.30-2.36 (m, 1H), 2.51 (ddd, J=1.4, 9.6, 17.8 Hz, 1H), 2.73-2.82 (m, 1H), 5.99 (d, J=1.8 Hz, 1H), 6.89 (d, J=1.8 Hz, 1H); $^{13}$C NMR (CDCl$_3$, 100 MHz) δ 26.0, 28.4 (3C), 29.0 (3C), 30.2, 34.4, 34.5, 85.5, 128.1, 135.8, 142.8, 143.7, 176.6, 199.0; HPLC (OD-H column), Hexane-EtOH=30:1 as eluent, 1.0 mL/min, $t_S$=8.7 min, $t_R$=10.3 min; HRMS (FAB) m/z calcd for C$_{17}$H$_{25}$O$_3$ (M+H) 277.1804. found 277.1809; [α]$^{27.2}_D$=−222.0 (c 1.1, CHCl$_3$) for 89% ee.

Product in Examples 73 and 74: yellow oil; TLC, $R_f$=0.73 (hexane-EtOAc=1:2); IR (CHCl$_3$) 3025, 1784, 1711, 1671, 1363, 1182 cm$^{-1}$; $^1$H NMR (CDCl$_3$, 400 MHz) δ 1.14 (d, J=6.8 Hz, 3H), 1.18 (d, J=6.8 Hz, 3H), 1.89 (s, 3H), 2.05-2.18 (m, 1H), 2.31 (ddd, J=1.8, 9.6, 13.2 Hz, 1H), 2.43-2.56 (m, 2H), 2.81 (ddd, J=9.6, 11.9, 17.6 Hz, 1H), 6.02 (d, J=6.4 Hz, 1H), 6.83 (d, J=6.4 Hz, 1H); HPLC (IA-3 column), Hexane- Product in Example 78: yellow solid; TLC, $R_f$=0.57 (hexane-EtOAc=1:1); IR (CHCl$_3$) 3025, 1793, 1678, 1574, 1168 cm$^{-1}$; $^1$H NMR (CDCl$_3$, 400 MHz) δ 2.07 (s, 3H), 2.13 (ddd, J=9.6, 11.4, 13.3 Hz, 1H), 2.22 (s, 3H), 2.35 (ddd, J=1.8, 10.1, 13.3 Hz, 1H), 2.57 (ddd, J=1.8, 9.6, 17.7 Hz, 1H), 2.82 (ddd, J=10.1, 11.4, 17.7 Hz, 1H), 6.02 (s, 1H); $^{13}$C NMR (CDCl$_3$, 100 MHz) δ 15.5, 22.7, 25.6, 29.8, 86.5, 120.8, 128.3, 142.6, 154.1, 175.9, 196.9; HPLC (OD-H column), Hexane-EtOH=4:1 as eluent, 1.0 mL/min, $t_R$=8.8 min, $t_S$=11.1 min; [α]$^{24.8}$=−204.2 (c 1.1, CHCl$_3$) for 77% ee.

[5-2] Oxidation of Phenol Compound in which OH Group is Bonded to Position 1 and OCH$_2$COOH is Bonded to Position 2

In Example 79, a phenol compound in which a OH group was bonded to position 1 and OCH$_2$COOH was bonded to position 2 was oxidized under the reaction condition described below. As a result, a spirolactone compound was obtained at a yield of 88% and 89% ee.

[Chem. 10]

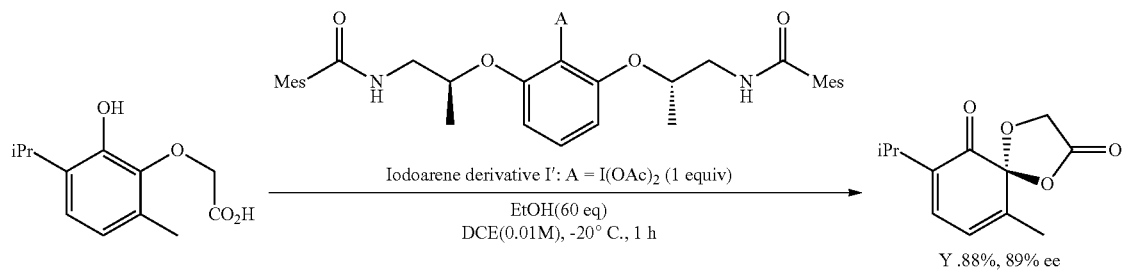

EtOH=4:1 as eluent, 1.0 mL/min, $t_S$=8.3 min, $t_R$=11.8 min.; [α]$^{24.9}_D$=−515.2 (c 0.3, CHCl$_3$) for 89% ee.

Product in Example 75: white solid; TLC, $R_f$=0.57 (hexane-EtOAc=1:2); IR (KBr) 2942, 1795, 1739, 1702, 1181 cm$^{-1}$; $^1$H NMR (CDCl$_3$, 400 MHz) δ 1.52-1.82 (m, 4H), 2.16 (ddd, J=9.6, 11.0, 13.3 Hz, 1H), 2.21-2.56 (m, 5H), 2.56 (ddd, J=2.3, 9.6, 17.6 Hz, 1H), 2.90 (ddd, J=9.6, 11.0, 17.6 Hz, 1H), 6.62 (s, 1H); $^{13}$C NMR (CDCl$_3$, 100 MHz) δ 20.8, 22.0, 22.4, 26.2, 30.8, 31.1, 83.4, 124.0, 131.5, 135.7, 148.0, 175.9, 196.4; HPLC (OD column), Hexane-EtOH=4:1 as eluent, 1.0 mL/min, $t_R$=9.7 min, $t_S$=11.0 min.; [α]$^{24.4}_D$=−45.4 (c 0.9, CHCl$_3$) for >99% ee (the optical purity was improved from 97% ee to more than 99% ee by one time of recrystallization).

Product in Example 76: yellow solid; TLC, $R_f$=0.66 (hexane-EtOAc=1:2); $^1$H NMR (CDCl$_3$, 400 MHz) δ 0.19 (s, 18H), 2.05 (ddd, J=9.6, 11.0, 13.2 Hz, 1H), 2.35 (ddd, J=2.3, 9.6, 13.2 Hz, 1H), 2.53 (ddd, J=2.3, 9.6, 17.5 Hz, 1H), 2.80 (ddd, J=9.6, 11.0, 17.5 Hz, 1H), 6.53 (d, J=1.8 Hz, 1H), 7.11 (d, J=1.8 Hz, 1H); HPLC (OD-H column), Hexane-EtOH=10:1 as eluent, 1.0 mL/min, $t_S$=4.6 min, $t_R$=5.2 min.

Product in Example 77: pale yellow oil; TLC, $R_f$=0.70 (hexane-EtOAc=1:1); IR (CHCl$_3$) 2965, 1787, 1675, 1651, 1185 cm$^{-1}$; $^1$H NMR (CDCl$_3$, 400 MHz) δ 1.07 (d, J=6.4 Hz, 6H), 1.93 (d, J=1.4 Hz, 3H), 2.07 (ddd, J=10.1, 11.4, 13.4 Hz, 1H), 2.30 (ddd, J=1.8, 9.6, 13.4 Hz, 1H), 2.53 (ddd, J=1.8, 9.6, 17.8 Hz, 1H), 2.77 (ddd, J=10.1, 11.4, 17.8 Hz, 1H), 2.87 (septet, J=6.4 Hz, 1H), 6.00 (dd, J=1.4, 6.4 Hz, 1H), 6.70 (d, J=6.4 Hz, 1H); $^{13}$C NMR (CDCl$_3$, 100 MHz) δ 17.1, 21.4, 21.5, 25.6, 26.2, 28.9, 87.6, 120.3, 135.2, 139.5, 146.1, 176.6, 199.5; HPLC (AS-3 column), Hexane-EtOH 4:1 as eluent, 1.0 mL/min, $t_S$=8.1 min, $t_R$=9.2 min; [α]$^{24.7}_D$=−477.9 (c 1.1, CHCl$_3$) for 91% ee.

Product in Example 79: yellow solid; TLC, $R_f$=0.57 (hexane-EtOAc=1:1); IR (CHCl$_3$) 3033, 1816, 1683, 1202 cm$^{-1}$; $^1$H NMR (CDCl$_3$, 400 MHz) δ 1.07 (d, J=6.8 Hz, 6H), 1.93 (s, 3H), 2.83 (septet, J=6.8 Hz, 1H), 4.38 (d, J=14.6 Hz, 1H), 4.64 (d, J=14.6 Hz, 1H), 6.18 (d, J=6.4 Hz, 1H), 6.65 (d, J=6.4 Hz, 1H); HPLC (AS-3 column), Hexane-EtOH=4:1 as eluent, 1.0 mL/min, $t_S$=5.9 min, $t_R$=7.3 min.; [α]$^{24.7}_D$=87.1 (c 0.4, CHCl$_3$) for 89% ee.

[6] Method for Manufacturing Cycloadduct

As indicated by Examples 80 to 85 shown in Table 8, various phenol compounds were converted to optically active spirolactone compounds through dearomatization type oxidation, and the resulting spirolactone compounds were subjected to a [4+2]cyclization reaction (Diels-Alder reaction) with methyl vinyl ketone (MVK), which was a dienophile, without being isolated. Consequently, an optically active cycloadduct having a complicated skeleton was highly enantioselectively obtained at a high yield at a stroke. The synthesis procedure of Example 80 will be described below as a typical example.

A solution in which phenol compound (35.4 mg, 0.1 mmol), Iodoarene derivative I (3.2 mg, 0.005 mmol, 5 percent by mole), and mCPBA (20.7 mg, 0.12 mmol, 1.2 equiv) were dissolved into dichloromethane (4.5 mL) and HFIP (0.5 mL) was agitated at −20° C. In this regard, a commercially available mCPBA (Aldrich, purity 77%) was refined to have a purity of more than 99% and was used as the mCPBA. After 18 hours were elapsed, MVK (82 μL, 1 mmol, 10 equiv) was added to the reaction solution, and the resulting reaction liquid was agitated at room temperature. After 12 hours were elapsed, the reaction mixed solution was poured into a $Na_2S_2O_3$ aqueous solution (5 mL) and a $NaHCO_3$ aqueous solution (5 ml), and extraction with $CHCl_3$ was performed two times. An organic layer was dried with anhydrous $MgSO_4$. The solvent was removed by distillation in a vacuum. The residue was refined by silica gel flash chromatography (dissolution medium hexane-EtOAc=10:1, 4:1 (v/v)) to obtain a product (15.4 mg, 0.073 mmol) at a yield of 73% and 96% ee. The purity of mCPBA (produced by Aldrich) employed was 77% and the purity of chloroform (produced by Nacalai) employed was 99%. Meanwhile, the other examples in Table 8 were performed in conformity with this synthesis procedure. Also, in the case where MVK was included in the system from the start together with the phenol compound instead of being added on the way, the reaction proceeded smoothly, and products were obtained at the same enantiomeric excess. However, it is preferable that MVK be added on the way because the chemical yield of the product becomes higher.

TABLE 8

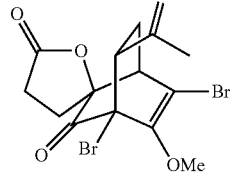

| | Phenol compound | Reaction condition | Product | Yield (%) | ee (%) |
|---|---|---|---|---|---|
| Example 80 | 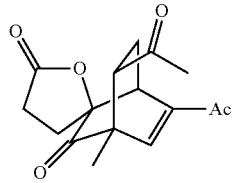 | mCPBA(1.2 equiv) *4<br>MVK(10 equiv)<br>Iodoarene I(5 mol %) *1<br>DCM/HFIP(9:1 v/v, 0.02M)<br>−20°C., 18 h | | 73 | 96 |
| Example 81 | | mCPBA(1.2 equiv) *4<br>MVK(10 equiv)<br>Iodoarene I(5 mol %) *1<br>DCM/HFIP(2:1 v/v, 0.02M)<br>−10°C., 24 h→rt, 12 h | | 60 | 74 |
| Example 82 | 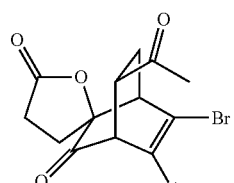 | mCPBA(1.2 equiv) *4<br>MVK(10 equiv)<br>Iodoarene I(5 mol %) *1<br>DCM/HFIP(9:1 v/v, 0.02M)<br>−10°C., 24 h→rt, 12 h | | 91 | 86 |
| Example 83 | | mCPBA(1.2 equiv) *4<br>MVK(10 equiv)<br>Iodoarene O(5 mol %) *2<br>DCM/HFIP(9:1 v/v, 0.02M)<br>−10°C., 24 h→rt, 12 h | 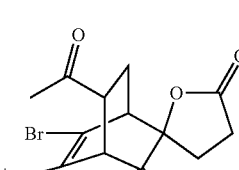 | 94 | 91 |

TABLE 8-continued

| | Phenol compound | Reaction condition | Product | Yield (%) | ee (%) |
|---|---|---|---|---|---|
| Example 84 | (1-hydroxy-tetrahydronaphthalene with CO₂H and Br substituents) | mCPBA(1.2 equiv) *4<br>MVK(10 equiv)<br>Iodoarene I(10 mol %) *1<br>DCE/CH₃NO₂(2:1 v/v, 0.02M)<br>−20°C., 18 h→rt, 12 h | (bicyclic product with Br) | 90 | 99 |
| Example 85 | | MVK(10 equiv)<br>Iodoarene I' (1 equiv) *3<br>DCE/CH₃NO₂(2:1 v/v, 0.01M)<br>−20° C., 2 h→rt, 12 h | | 70 | 99 |

*1 Iodoarene I:

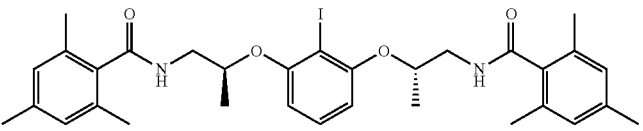

*2 Iodoarene O:

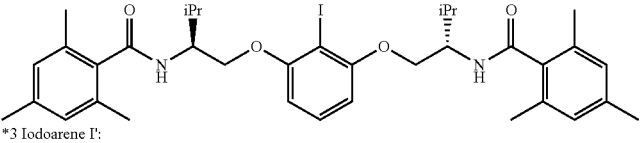

*3 Iodoarene I':

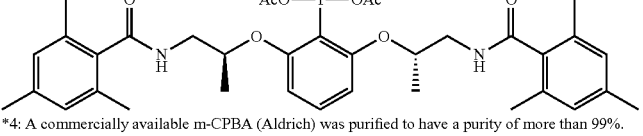

*4: A commercially available m-CPBA (Aldrich) was purified to have a purity of more than 99%.

The spectrum data of the products obtained in Examples 80 to 85 are as described below.

Product in Example 80: white solid; TLC, $R_f$=0.67 (hexane-EtOAc=1:2); IR (CHCl₃) 2943, 1793, 1755, 1725, 1629, 1361, 1168 cm⁻¹; ¹H NMR (CDCl₃, 400 MHz) δ 1.93 (ddd, J=2.8, 6.4, 12.8 Hz, 1H), 2.23 (ddd, J=8.7, 10.1, 13.4 Hz, 1H), 2.30 (s, 3H), 2.42 (ddd, J=5.0, 10.1, 13.4 Hz, 1H), 2.56 (ddd, J=2.8, 9.6, 12.8 Hz, 1H), 2.66 (ddd, J=5.0, 10.1, 17.8 Hz, 1H), 2.93 (ddd, J=8.7, 10.1, 17.8 Hz, 1H), 3.21 (t, J=2.8 Hz, 1H), 3.44 (dd, J=6.4, 9.6 Hz, 1H), 3.92 (s, 3H); ¹³C NMR (CDCl₃, 100 MHz) δ 28.3, 28.4, 29.8, 32.3, 50.7, 52.3, 61.5, 69.8, 81.3, 98.1, 147.1, 174.9, 193.9, 205.5; HPLC (IA-3 column), Hexane-EtOH=4:1 as eluent, 1.0 mL/min, $t_S$=20.2 min, $t_R$=21.9 min.; $[α]^{25.2}_D$=95.5 (c 2.8, CHCl₃) for 96% ee.

Product in Example 81: white solid; TLC, $R_f$=0.50 (hexane-EtOAc=1:1); ¹H NMR (CDCl₃, 400 MHz) δ 1.40 (s, 3H), 1.41-1.44 (m, 1H), 1.82 (ddd, J=8.7, 10.1, 13.1 Hz, 1H), 2.03 (ddd, J=5.0, 10.1, 18.2 Hz, 1H), 2.15 (s, 3H), 2.38 (s, 3H), 2.50-2.83 (m, 3H), 3.09 (dd, J=6.4, 10.5 Hz, 1H), 3.80 (d, J=2.3 Hz, 1H), 6.97 (s, 1H); HPLC (OD-H column), Hexane-EtOH=4:1 as eluent, 1.0 mL/min, $t_R$=14.1 min, $t_S$=16.6 min.

Product in Examples 82 and 83; Colorless oil; TLC, $R_f$=0.70 (hexane-EtOAc=1:2); IR (CHCl₃) 2966, 1786, 1734, 1719, 1364, 1140 cm⁻¹; ¹H NMR (CDCl₃, 400 MHz) δ 0.90 (d, J=6.9 Hz, 3H), 0.94 (d, J=6.9 Hz, 3H), 2.14-2.23 (m, 2H), 2.23 (s, 3H), 2.30 (ddd, J=5.5, 10.1, 13.3 Hz, 1H), 2.64 (ddd, J=5.5, 10.1, 17.9 Hz, 1H), 2.82-2.97 (m, 2H), 3.68 (d, J=1.4 Hz, 1H); ¹³C NMR (CDCl₃, 100 MHz) δ 19.2, 20.0, 22.9, 28.5, 28.8, 29.3, 31.7, 46.3, 50.6, 52.5, 81.6, 116.6, 140.8, 175.6, 202.5, 204.4; HPLC (OD-H column), Hexane-EtOH=4:1 as eluent, 1.0 mL/min, $t_S$=12.6 min, $t_R$=32.2 min.; $[\alpha]^{23.7}_D$=80.7 (c 1.3, CHCl$_3$) for 93% ee.

Product in Examples 84 and 85; white solid; TLC, $R_f$=0.50 (hexane-EtOAc=1:1); IR (KBr) 2939, 1789, 1733, 1710, 1363, 1169 cm$^{-1}$; $^1$H NMR (CDCl$_3$, 400 MHz) δ 1.22-1.40 (m, 2H), 1.50-1.70 (m, 3H), 1.74 (ddd, J=2.8, 6.4, 13.2 Hz, 1H), 2.12-2.20 (m, 1H), 2.12 (s, 3H), 2.26-2.35 (m, 3H), 2.43-2.70 (m, 3H), 2.86 (ddd, J=8.3, 10.1, 18.3 Hz, 1H), 2.96 (dd, J=6.4, 10.1 Hz, 1H), 3.17 (t, J=2.8 Hz, 1H); $^{13}$C NMR (CDCl$_3$, 100 MHz) δ 20.9, 21.6, 24.1, 27.2, 28.5, 28.6, 29.4, 31.3, 51.1, 51.5, 55.3, 81.8, 114.8, 137.7, 175.8, 202.9, 206.6; HPLC (AS-3 column), Hexane-EtOH=4:1 as eluent, 1.0 mL/min, $t_R$=17.4 min, $t_S$=18.7 min.; $[\alpha]^{29.7}_D$=151.2 (c 1.1, CHCl$_3$) for 99% ee.

The present application claims priority from Japanese Patent Application No. 2011-052572 filed on Mar. 10, 2011, the entire contents of which are incorporated in the present specification by reference.

INDUSTRIAL APPLICABILITY

The present invention can be utilized mainly for a pharmaceutical chemical industry and can be utilized in production of, for example, natural products, drugs, pesticides, and cosmetics, which have optically active spirolactone skeletons.

The invention claimed is:

1. An iodoarene derivative represented by Formula (a):

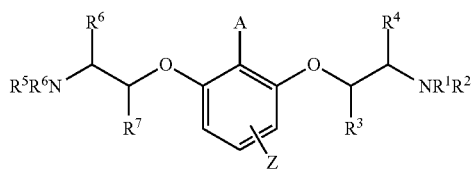

(a)

where:
A represents a monovalent iodine atom or a trivalent iodine atom having two ligands,
R$^1$, R$^4$, R$^5$, and R$^8$ represent a hydrogen atom,
R$^2$ and R$^6$ represent an aryl group, an alkoxycarbonyl group, an arylcarbonyl group, or an arylsulfonyl group,
R$^3$ and R$^7$ represent an alkyl group, and both configurations of asymmetric carbon atoms bonding to R$^3$ and R$^7$ are R or both the configurations are S, and
Z represents a hydrogen atom or an alkyl group.

2. An iodoarene derivative represented by Formula (a):

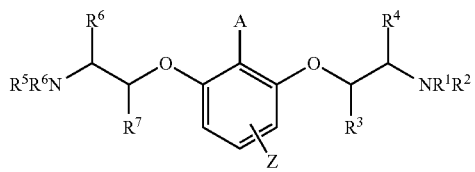

(a)

where:
A represents a monovalent iodine atom,
R$^1$, R$^3$, R$^5$, and R$^7$ represent a hydrogen atom,
R$^2$ and R$^6$ represent an arylcarbonyl group,
R$^4$ and R$^8$ represent an alkyl group, an arylmethyl group, or an aryl group, and both configurations of asymmetric carbon atoms bonding to R$^4$ and R$^8$ are R or both the configurations are S, and
Z represents a hydrogen atom.

3. A method for manufacturing an optically active spirolactone compound, the method comprising:
mixing a phenol derivative, the iodoarene derivative according to claim 1 in which A represents a monovalent iodine atom, and a peroxycarboxylic acid to induce a reaction to produce the optically active spirolactone compound in which an OH group of the phenol derivative is converted to an oxo group (=O) and dearomatized to have spiro-bonding of lactone rings, the iodoarene derivative being present in a catalyst quantity relative to a quantity of the phenol derivative, and the peroxycarboxylic acid being present in an quantity more than or equal to a stoichiometric quantity relative to the quantity of the phenol derivative,
wherein:
the phenol derivative comprises two adjacent carbon atoms, a first carbon atom and a second carbon atom, the first carbon atom constituting an aromatic ring bonded to an OH group, and the second carbon atom being bonded to -Q-COOH, where:
Q represents —(CH$_2$)$_n$—, —O(CH$_2$)$_m$—, —CH$_2$OCH$_2$—, —(CH$_2$)$_k$CH=CH—, —(CH$_2$)$_k$C=C—, —OCH=CH—, or —OC=C—,
n represents 2 or 3,
m represents 1 or 2,
k represents 0 or 1,
the C=C group of —(CH$_2$)$_k$C=C— and —OC=C— constitutes part of a benzene ring or a naphthalene ring, and
the CH=CH group of —OCH=CH— and —(CH$_2$)$_k$CH=CH— is cis, and
the peroxycarboxylic acid is configured to oxidize the iodoarene derivative to convert the iodoarene derivative to a hypervalent iodine compound.

4. A method for manufacturing an optically active spirolactone compound, the method comprising:
mixing a phenol derivative and the iodoarene derivative according to claim 1 in which A represents a trivalent iodine atom to induce a reaction to produce the optically active spirolactone compound in which an OH group of the phenol derivative is converted to an oxo group (=O) and dearomatized to have spiro-bonding of lactone rings, the iodoarene derivative being present in a quantity that is more than or equal to a stoichiometric quantity relative to a quantity of the phenol derivative,
wherein the phenol derivative comprises two adjacent carbon atoms, a first carbon atom and a second carbon atom, the first carbon atom constituting an aromatic ring bonded to an OH group, and the second carbon atom being bonded to -Q-COOH, where:
Q represents —(CH$_2$)$_n$—, —O(CH$_2$)$_m$—, —CH$_2$OCH$_2$—, —(CH$_2$)$_k$CH=CH—, —(CH$_2$)$_k$C=C—, —OCH=CH—, or —OC=C—
n represents 2 or 3,
m represents 1 or 2,
k represents 0 or 1,
the C=C group of —(CH$_2$)$_k$C=C— and —OC=C— constitutes part of a benzene ring or a naphthalene ring, and
the CH=CH group of —OCH=CH— and —(CH$_2$)$_k$CH=CH— is cis.

5. The method for manufacturing an optically active spirolactone compound according to claim 3, wherein the phenol derivative is a naphthol compound or a phenol compound in which an OH group is bonded to position 1 and -Q-COOH is bonded to position 2.

6. The method for manufacturing an optically active spirolactone compound according to claim 4, wherein the phenol derivative is a naphthol compound or a phenol compound in which an OH group is bonded to position 1 and -Q-COOH is bonded to position 2.

7. The method for manufacturing an optically active spirolactone compound according to claim 5 further comprising mixing an alcohol with the phenol derivative, the iodoarene derivative, and the peroxycarboxylic acid.

8. The method for manufacturing an optically active spirolactone compound according to claim 3, wherein the phenol derivative is a naphthol compound in which -Q-COOH is bonded to position 1 and an OH group is bonded to position 2.

9. The method for manufacturing an optically active spirolactone compound according to claim 3 further comprising mixing the phenol derivative, the iodoarene derivative, and the peroxycarboxylic acid with a reaction solvent, the reaction solvent consisting of one or more selected from the group consisting of a halogenated alkane, a nitroalkane, an ester, and a fluorine based alcohol.

10. A method for manufacturing an optically active cycloadduct, the method comprising obtaining an optically active spirolactone compound by the method according to claim 3 without isolation of the spirolactone, and reacting the spirolactone with a dienophile to produce an optically active [4+2]cycloadduct.

11. The method for manufacturing an optically active spirolactone compound according to claim 6 further comprising mixing an alcohol with the phenol derivative, the iodoarene derivative, and the peroxycarboxylic acid.

12. The method for manufacturing an optically active spirolactone compound according to claim 4, wherein the phenol derivative is a naphthol compound in which -Q-COOH is bonded to position 1 and an OH group is bonded to position 2.

13. The method for manufacturing an optically active spirolactone compound according to claim 4 further comprising mixing the phenol derivative, the iodoarene derivative, and the peroxycarboxylic acid with a reaction solvent, the reaction solvent consisting of one or more selected from the group consisting of a halogenated alkane, a nitroalkane, an ester, and a fluorine based alcohol.

14. A method for manufacturing an optically active cycloadduct, the method comprising obtaining an optically active spirolactone compound by the method according to claim 4 without isolation of the spirolactone, and reacting the spirolactone with a dienophile to produce an optically active [4+2]cycloadduct.

* * * * *